US012630852B2

(12) United States Patent
Lehmann et al.

(10) Patent No.: US 12,630,852 B2
(45) Date of Patent: May 19, 2026

(54) MODIFIED STEROL ACYLTRANSFERASES

(71) Applicant: DSM IP ASSETS B.V., Heerlen (NL)

(72) Inventors: Otto Martin Lehmann, Kaiseraugst
(CH); Harald Pichler, Graz (AT);
Holly Stolterfoht, Graz (AT)

(73) Assignee: DSM IP ASSETS B.V., Heerlen (NL)

( * ) Notice: Subject to any disclaimer, the term of this
patent is extended or adjusted under 35
U.S.C. 154(b) by 1034 days.

(21) Appl. No.: 17/050,639

(22) PCT Filed: May 21, 2019

(86) PCT No.: PCT/EP2019/063078
§ 371 (c)(1),
(2) Date: Oct. 26, 2020

(87) PCT Pub. No.: WO2019/224188
PCT Pub. Date: Nov. 28, 2019

(65) Prior Publication Data
US 2021/0095325 A1     Apr. 1, 2021

(30) Foreign Application Priority Data
May 22, 2018     (CH) ..................................... 00628/18

(51) Int. Cl.
*C12P 33/00*     (2006.01)
*C12N 9/02*     (2006.01)
*C12N 9/10*     (2006.01)

(52) U.S. Cl.
CPC .............. *C12P 33/00* (2013.01); *C12N 9/001*
(2013.01); *C12N 9/1029* (2013.01); *C12Y*
*103/01072* (2013.01); *C12Y 203/01026*
(2013.01)

(58) Field of Classification Search
CPC ....... C12P 33/00; C12N 9/001; C12N 9/1029;
C12Y 103/01072; C12Y 203/01026
See application file for complete search history.

(56) References Cited

U.S. PATENT DOCUMENTS 7,608,421 B2     10/2009  Lang et al.

FOREIGN PATENT DOCUMENTS

WO          03/064650          8/2003
WO          2011/067144        6/2011
WO          2017/108799        6/2017

OTHER PUBLICATIONS

Kessi-Pérez, Eduardo I., et al. "Yeast as a biological platform for
vitamin D production: A promising alternative to help reduce
vitamin D deficiency in humans." Yeast 39.9 (2022): 482-492 (Year:
2022).*

(Continued)

*Primary Examiner* — Thane Underdahl
*Assistant Examiner* — Mary A Crum
(74) *Attorney, Agent, or Firm* — NIXON &
VANDERHYE, PC

(57) ABSTRACT

The present invention is related to modified sterol acyltrans-
ferase enzymes with improved activity and/or specificity
towards acylation of the vitamin D3 precursor 7-dehydro-
cholesterol (7-DHC) to be used in biotechnological produc-
tion of vitamin D3. The invention further relates to a host
strain expressing said modified enzymes and their use in a
process for production of vitamin D3 or derivatives and/or
metabolites thereof.

Figure 1:
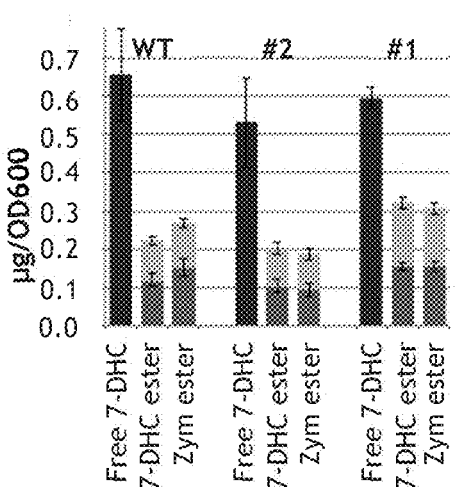
Figure 1:
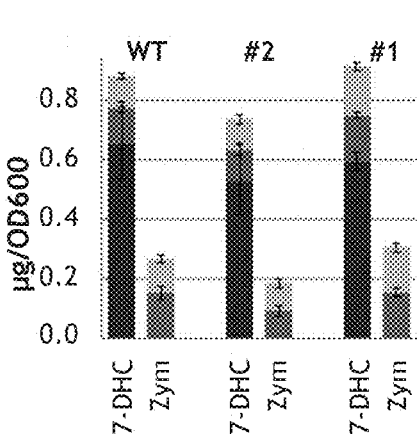
Figure 1:
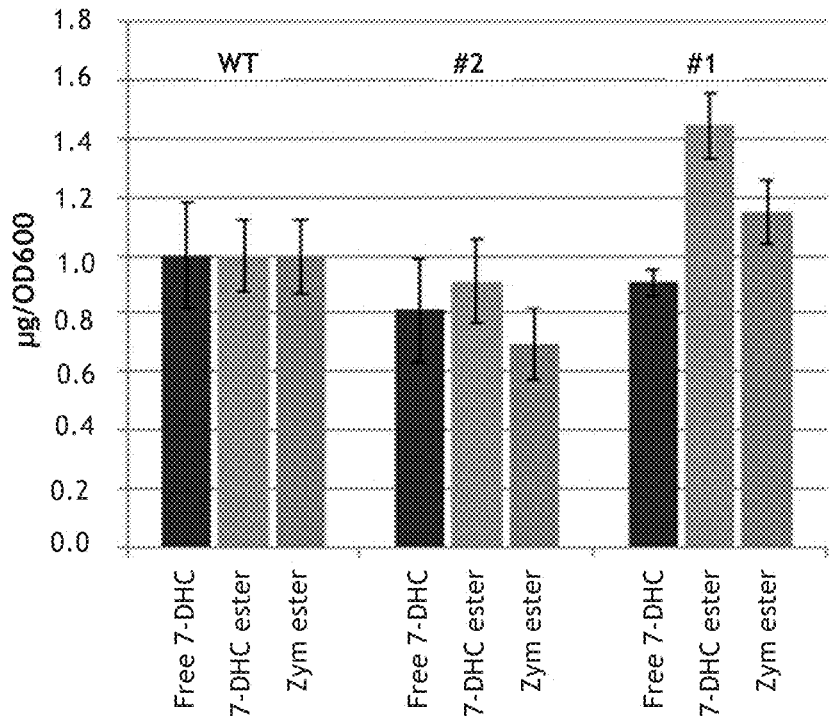

19 Claims, 10 Drawing Sheets
Specification includes a Sequence Listing.

(56) References Cited

OTHER PUBLICATIONS

Lazar, Eliane, et al. "Transforming growth factor α: mutation of aspartic acid 47 and leucine 48 results in different biological activities." Molecular and Cellular Biology 8.3 (1988): 1247-1252 (Year: 1988) (Year: 1988).*

Burgess, Wilson H., et al. "Possible dissociation of the heparin-binding and mitogenic activities of heparin-binding (acidic fibroblast) growth factor-1 from its receptor-binding activities by site-directed mutagenesis of a single lysine residue." The Journal of Cell Biology 111.5 (1990): 2129-2138 (Year: 1990).*

Bowie, James U., et al. "Deciphering the message in protein sequences: tolerance to amino acid substitutions." Science 247.4948 (1990): 1306-1310 (Year: 1990).*

International Search Report for PCT/EP2019/063078 dated Aug. 12, 2019, 5 pages.

Written Opinion of the ISA for PCT/EP2019/063078 dated Aug. 12, 2019, 7 pages.

Yu et al., "Molecular Cloning and Characterization of Two Isoforrns of Saccharomyces cerevisiae Acyl-CoA:Sterol Acyltransferase", The Journal of Biological Chemistry, Sep. 27, 1996, vol. 271, No. 39, XP002094336, pp. 24157-24163 (7 total pages).

Wriessnegger et al., "Yeast metabolic engineering—Targeting sterol metabolism and terpenoid formation", Progress in Lipid Research, Apr. 6, 2013, vol. 52, No. 3, XP028553555, pp. 277-293 (17 total pages).

Zweytick et al., "Contribution of Are1p and Are2p to steryl ester synthesis in the yeast Saccharomyces cerevisiae", European Journal of Biochemistry, Feb. 1, 2000, vol. 267, No. 4, XP055059359, pp. 1075-1082, (8 total pages).

Das et al, "Identification of putative active site residues of ACAT enzymes," Journal of Lipid Research, vol. 49, pp. 1770-1781, 2008.

Guo et al, "Identification of potential substrate-binding sites in yeast and human acyl-CoA sterol acyltransferases by mutagenesis of conserved sequences," Journal of Lipid Research, vol. 42, pp. 1282-1291, 2001.

Yang, et al, "Functional Expression of a cDNA to Human Acyl-coenzyme, A:Cholesterol Acyltransferase in Yeast," The Journal of Biological Chemistry, The American Society for Biochemistry and Molecular Biology, Inc., vol. 272, No. 7, Issue of Feb. 14, pp. 3980-3985, 1997.

* cited by examiner

A.

B.

C.

A.

B.

C.

A.

B.

C.

A.

B.

C.

A.

B.

C.

A.

B.

C.

A.

B.

C.

A.

B.

C.

MODIFIED STEROL ACYLTRANSFERASES

CROSS-REFERENCE TO RELATED APPLICATIONS

This application is the U.S. national phase of International Application No. PCT/EP2019/063078 filed May 21, 2019 which designated the U.S. and claims priority to CH 00628/18 filed May 22, 2018, the entire contents of each of which are hereby incorporated by reference.

REFERENCE TO SEQUENCE LISTING SUBMITTED ELECTRONICALLY

The content of the electronically submitted sequence listing (Name: 4662-4079_Sequence_Listing.txt; Size: 26 kilobytes) filed with the application is incorporated herein by reference in its entirety.

The present invention is related to modified sterol acyltransferase enzymes with improved activity and/or specificity towards acylation of the vitamin D3 precursor 7-dehydrocholesterol (7-DHC) to be used in biotechnological production of vitamin D3. The invention further relates to a host strain expressing said modified enzymes and their use in a process for production of vitamin D3 or derivatives and/or metabolites thereof.

Vitamin D3 (also known as cholecalciferol or calciol) can be synthesized in the skin of mammals from provitamin D3 (also known as 7-dehydrocholesterol or 7-DHC) which is product of cholesterol biosynthesis upon exposure to UV light, whereby 7-DHC is photochemically converted into provitamin D3, which isomerizes at body temperature to the biologically active form vitamin D3. In the liver, vitamin D3 is converted to the biologically inactive 25-hydroxyvitamin D3 (also known as calcidiol, calcifediol, 25-hydroxycholecalciferol, 25-0H-D3 or HyD), which is the major circulating form of vitamin D3. Further hydroxylation occurs in the kidney.

For industrial production of vitamin D3, both chemical and biotechnological synthesis is (in principle) available. Chemical synthesis starts with cholesterol isolated from e.g. wool fat which is dehydrogenated into 7-DHC, an important intermediate in both chemical and biotechnological synthesis. Through exposure by UV-light and further purification/extraction steps 7-DHC is converted into vitamin D3. Modified yeast stains can be used for biosynthesis of 7-DHC, wherein acetyl-CoA is converted in a multi-step enzymatic process into 7-DHC. Said enzymatic conversion takes place in the endoplasmatic reticulum of the yeast. Excessive amounts of sterols, including 7-DHC and precursors thereof, not required in cellular membranes, are toxic to the yeast and are thus stored as steryl esters into intracellular organelles (so-called lipid bodies) from which they can be further isolated. The equilibrium between free sterols and those stored in the lipid bodies (mainly in the form of steryl esters) is triggered via the action of several proteins (enzymes), including action of sterol acyltransferases. In yeast, particularly *Saccharomyces cerevisiae*, ester formation of sterols is mainly carried out by the two sterol acyltransferases Are1p and Are2p.

Due to the unspecific action of said sterol acyltransferase enzymes, the steryl ester pool which is stored within the lipid bodies is relatively diverse, including but not limited to e.g. esters of ergosterol, zymosterol, lanosterol, lathosterol, cholesta-5,7,24(25)-trienol, or 7-DHC. Since only cholesta-5,7,24(25)-trienol, a precursor for 7-DHC, and not zymosterol can be used for vitamin D3 synthesis, there is a need for either selective storage of specific esters, such as e.g. esters of 7-DHC, into the lipid bodies and/or for increasing the turnover of intermediates of 7-DHC produced by such a yeast strains which are further converted to vitamin D3 and/or derivatives or metabolites thereof. A particular metabolite which is also in focus of the present invention is 25-hydroxyvitamin D3.

Thus, it is an ongoing task to generate host cells, such as yeast capable of producing sterols, with high productivity/specificity for 7-DHC and/or reduced accumulation of side-products/intermediates including zymosterol, lanosterol or lathosterol, in particular esters of such intermediates stored in the lipid bodies.

Surprisingly, we now found that the specificity and/or activity of the sterol acyltransferase activity in the host cell can be shifted via introduction of certain amino acid substitutions in the sequence of ARE2 and/or ARE1, which will lead to higher productivity of the host cell towards 7-DHC as important intermediate in vitamin D3 production.

Thus, the present invention is directed to a modified enzyme with sterol acyltransferase activity, i.e. modified sterol acyltransferases, particularly activity of sterol acyltransferase isoform Are1p and/or Are2p, comprising one or more amino acid substitution(s) at (a) position(s) corresponding to residues selected from the group consisting of 11, 281, 366, 442, 551, 554, 572, 624, 626, 627, 636, and combinations thereof in the polypeptide according to SEQ ID NO:1, said modified enzyme has increased specificity for 7-DHC over side-products/intermediates including zymosterol and/or increased activity towards ester formation, including esters of 7-DHC.

The polypeptide according to SEQ ID NO:1, showing ARE2 activity, including polynucleotides encoding said polypeptide, has been isolated from *Saccharomyces cerevisiae*. The polypeptide according to SEQ ID NO:3, showing ARE1 activity, including polynucleotides encoding said polypeptide, has been isolated from *Saccharomyces cerevisiae*.

The terms "sterol acyltransferase", "acyltransferase", "ARE", "enzyme having acyltransferase activity" or just "enzyme" are used interchangeably herein and refer to enzymes [EC 2.3.1.26], i.e. acyltransferases transferring fatty acyl groups from one molecule to another. Such transfer or enzymatic activity can be measured by means known to the skilled person. Sterol acyltransferases have been isolated from different origins, including mammals, yeast or plants. Both ARE1 and ARE2 are capable of acylating sterols such as e.g. zymosterol and/or 7-DHC to the respective esters. As used herein, a "modified" enzyme, i.e. modified acyltransferase, has a preferred activity and/or specificity towards esterification of 7-DHC compared to esterification of e.g. zymosterol and/or improved formation of total sterol esters, including e.g. 7-DHC or zymosterol. Preferred acyltransferase isoforms are Are2p or Are1p. A "non-modified" sterol acyltransferase, particularly ARE1 and ARE2, as used herein refers to the respective endogenous enzymes not carrying one or more amino acid substitution(s) as defined herein.

As used herein, a host cell carrying a modified sterol acyltransferase activity as defined herein, particularly ARE2 and/or ARE1 comprising one or more amino acid substitution(s) as defined herein, is referred to as "modified" host cell. The respective host cell carrying a non-modified sterol acyltransferase activity, i.e. encoding the wild-type ARE2 and/or ARE1 genes, is referred to as "non-modified" host cell.

As used herein, the terms "zymosterol", "lanosterol", "lathosterol", "cholesta-5,8,24(25)-trienol", "cholesta-5,7, 24(25)-trienol", or "7-DHC" specifying vitamin D3 intermediates include both the free form and the ester form of said compounds. As used herein, a sterol mix contains 7-DHC and "side-products" or intermediates, including but not limited to zymosterol, lanosterol, lathosterol, cholesta-5,8,24(25)-trienol, or cholesta-5,7,24(25)-trienol.

As used herein, a "cholesterol-producing yeast" cannot produce ergosterol anymore but cholesterol products, including, but not limited to cholesta-5,7,24(25)-trienol, cholesta-5,8,24(25)-trienol, cholesta-7,24(25)-dienol, 7-DHC or zymosterol. Particularly, this might be achieved via introduction of erg5erg6 double-knock out.

Particularly, the modification corresponds to a modified activity of sterol acyltransferase 2 and/or 1, i.e. ARE2 and/or ARE1 activity, comprising amino acid substitution(s), wherein preferably the at least one amino acid substitution at (a) position(s) corresponding to residues selected from the group consisting of 11, 281, 366, 442, 551, 554, 572, 624, 626, 627, 636 and combinations thereof in the polypeptide according to SEQ ID NO:1 corresponds to (an) amino acid substitution(s) of E11 and/or L281 and/or D366 and/or I442 and/or H551 and/or H554 and/or F572 and/or F624 and/or L626 and/or G627 and/or C636. More preferably, the modification corresponds to a modified ARE2 activity, even more preferably a modified polypeptide according to SEQ ID NO:1, wherein at least one amino acid substitution at (a) position(s) selected from the group consisting of 11, 281, 366, 442, 551, 554, 572, 624, 626, 627, 636, and combinations thereof have been introduced. Preferably, the enzyme having modified ARE2 and/or ARE1 activity are originated from Saccharomyces, such as S. cerevisiae.

In one embodiment, the modified enzyme as defined herein, in particular modified ARE2 and/or ARE1 activity, comprises an amino acid substitution at a position corresponding to residue 11 in the polypeptide according to SEQ ID NO:1, preferably substitution of glutamic acid by glycine (E11G). The described amino acid substitution at a position corresponding to residue E11G in SEQ ID NO:1 might be combined with further substitutions as defined herein, i.e. substitutions on one or more position(s) corresponding to amino acid residue(s) 281, 366, 442, 551, 554, 572, 624, 626, 627 and/or 636 in the polypeptide according to SEQ ID NO:1 and as described herein. Preferably, the amino acid substitution at a position corresponding to residue E11G in SEQ ID NO:1 might be combined with further substitution(s), such as amino acid substitution(s) at position(s) corresponding to F624L, G627D, D366V, C636S, and/or I442V in SEQ ID NO:1, more preferably are combinations of substitutions corresponding to residues E11G-F624L, E11G-G627D, E11G-D366V-C636S, E11G-D366V-G627D-C636S, E11G-D366V-F624L-C636S, E11G-D366V-I442V-F624L-C636S or E11G-D366V-I442V-G627D-C636S in SEQ ID NO:1, with most preferred combinations selected from E11G-D366V-C636S, E11G-D366V-G627D-C636S, E11G-D366V-F624L-C636S, E11G-D366V-I442V-G627D-C636S or E11G-D366V-I442V-F624L-C636S. Using a cholesterol-producing yeast carrying such modified enzymes, in particular enzymes according to SEQ ID NO:1 comprising one of said amino acid substitution(s), enzyme specificity could be increased in the range of at least about 3 to 5-times compared to using a non-modified yeast as defined herein.

In one embodiment, the modified enzyme as defined herein, in particular modified ARE2 and/or ARE1 activity, comprises an amino acid substitution at a position corresponding to residue 281 in the polypeptide according to SEQ ID NO:1, preferably substitution of leucine by isoleucine (L281I). The described amino acid substitution at a position corresponding to residue L281I in SEQ ID NO:1 might be combined with further substitutions as defined herein, i.e. substitutions on one or more position(s) corresponding to amino acid residue(s) 11, 366, 442, 551, 554, 572, 624, 626, 627 and/or 636 in the polypeptide according to SEQ ID NO:1 and as described herein. Using a cholesterol-producing yeast carrying such modified enzymes, in particular enzymes according to SEQ ID NO:1 comprising one of said amino acid substitution(s), relative ester formation could be increased in the range of at least about 1.5-times compared to using a non-modified yeast as defined herein.

In one embodiment, the modified enzyme as defined herein, in particular modified ARE2 and/or ARE1 activity, comprises an amino acid substitution at a position corresponding to residue 366 in the polypeptide according to SEQ ID NO:1, preferably substitution of aspartic acid by valine (D366V). The described amino acid substitution at a position corresponding to residue D366V in SEQ ID NO:1 might be combined with further substitutions as defined herein, i.e. substitutions on one or more position(s) corresponding to amino acid residue(s) 11, 281, 366, 442, 551, 554, 572, 624, 626, 627, and/or 636 in the polypeptide according to SEQ ID NO:1 and as described herein. Using a cholesterol-producing yeast carrying such modified enzymes, in particular enzymes according to SEQ ID NO:1 comprising one of said amino acid substitution(s), enzyme specificity could be increased in the range of at least about 3-times compared to using a non-modified yeast as defined herein.

In another embodiment, the modified enzyme as defined herein, in particular modified ARE2 and/or ARE1 activity, comprises an amino acid substitution at a position corresponding to residue 442 in the polypeptide according to SEQ ID NO:1, preferably substitution of isoleucine by valine (I442V). The described amino acid substitution at a position corresponding to residue I442V in SEQ ID NO:1 might be combined with further substitutions as defined herein, i.e. substitutions on one or more position(s) corresponding to amino acid residue(s) 11, 281, 366, 551, 554, 572, 624, 626, 627, and/or 636 in the polypeptide according to SEQ ID NO:1 and as described herein. Preferably, the amino acid substitution at a position corresponding to residue I442V in SEQ ID NO:1 might be combined with further substitutions, such as amino acid substitutions at position(s) corresponding to F624L, L626F and/or G627D in SEQ ID NO:1, more preferably are combinations of substitutions corresponding to residues I442V-L626F, I442V-G627D, I442V-F624L-L626F or I442V-L626F-G627D in SEQ ID NO:1, with most preferred combinations selected from I442V-G627D, I442V-F624L-L626F or I442V-L626F-G627D. Using a cholesterol-producing yeast carrying such modified enzymes, in particular enzymes according to SEQ ID NO:1 comprising one of said amino acid substitution(s), enzyme specificity could be increased in the range of at least about 2.2 to 4.5-times compared to using a non-modified yeast as defined herein.

In a further embodiment, the modified enzyme as defined herein, in particular modified ARE2 and/or ARE1 activity, comprises an amino acid substitution at a position corresponding to residue 551 in the polypeptide according to SEQ ID NO:1, preferably substitution of histidine by tyrosine (H551Y). The described amino acid substitution at a position corresponding to residue H551Y in SEQ ID NO:1 might be combined with further substitutions as defined herein, i.e. substitutions on one or more position(s) corresponding to amino acid residue(s) 11, 281, 366, 442, 554, 572, 624, 626, 627, and/or 636 in the polypeptide according to SEQ ID NO:1 and as described herein. Using a cholesterol-producing yeast carrying such modified enzymes, in particular enzymes according to SEQ ID NO:1 comprising one of said amino acid substitution(s), enzyme specificity could be increased in the range of at least about 1.7-times compared to using a non-modified yeast as defined herein.

In one embodiment, the modified enzyme as defined herein, in particular modified ARE2 and/or ARE1 activity, comprises an amino acid substitution at a position corresponding to residue 554 in the polypeptide according to SEQ ID NO:1, preferably substitution of histidine by glutamine (H554Q). The described amino acid substitution at a position corresponding to residue H554Q in SEQ ID NO:1 might be combined with further substitutions as defined herein, i.e. substitutions on one or more position(s) corresponding to amino acid residue(s) 11, 281, 366, 442, 551, 572, 624, 626, 627, and/or 636 in the polypeptide according to SEQ ID NO:1 and as described herein. Preferably, the amino acid substitution at a position corresponding to residue H554Q in SEQ ID NO:1 might be combined with further substitutions, such as amino acid substitutions at position(s) corresponding to F624L, F572L and/or G627D in SEQ ID NO:1, more preferably are combinations of substitutions corresponding to residues H554Q-F572L-F624L or H554Q-F572L-G627D in SEQ ID NO:1. Using a cholesterol-producing yeast carrying such modified enzymes, in particular enzymes according to SEQ ID NO:1 comprising one of said amino acid substitution(s), enzyme specificity could be increased in the range of at least about 1.4 to over 12-times compared to using a non-modified yeast as defined herein.

In another embodiment, the modified enzyme as defined herein, in particular modified ARE2 and/or ARE1 activity, comprises an amino acid substitution at a position corresponding to residue 572 in the polypeptide according to SEQ ID NO:1, preferably substitution of phenylalanine by leucine (F572L). The described amino acid substitution at a position corresponding to residue F572L in SEQ ID NO:1 might be combined with further substitutions as defined herein, i.e. substitutions on one or more position(s) corresponding to amino acid residue(s) 11, 281, 366, 442, 551, 554, 624, 626, 627, and/or 636 in the polypeptide according to SEQ ID NO:1 and as described herein. Using a cholesterol-producing yeast carrying such modified enzymes, in particular enzymes according to SEQ ID NO:1 comprising one of said amino acid substitution(s) as defined above, enzyme specificity could be increased in the range of at least about 1.7-times compared to using a non-modified yeast as defined.

In one embodiment, the modified enzyme as defined herein, in particular modified ARE2 and/or ARE1 activity, comprises an amino acid substitution at a position corresponding to residue 624 in the polypeptide according to SEQ ID NO:1, preferably substitution of phenylalanine by leucine (F624L), which corresponds to substitution of F592L in the polypeptide according to SEQ ID NO:3. The described amino acid substitution at a position corresponding to residue F624L in SEQ ID NO:1 might be combined with further substitutions as defined herein, i.e. substitutions on one or more position(s) corresponding to amino acid residue(s) 11, 281, 366, 442, 551, 554, 572, 626, 627, and/or 636 in the polypeptide according to SEQ ID NO:1 and as described herein. Using a cholesterol-producing yeast carrying such modified enzymes, in particular enzymes according to SEQ ID NO:1 comprising one of said amino acid substitution(s), enzyme specificity could be increased in the range of at least about 3.1-times compared to using a non-modified yeast as defined herein.

In one embodiment, the modified enzyme as defined herein, in particular modified ARE2 and/or ARE1 activity, comprises an amino acid substitution at a position corresponding to residue 626 in the polypeptide according to SEQ ID NO:1, preferably substitution of leucine by phenylalanine (L626F). The described amino acid substitution at a position corresponding to residue L626F in SEQ ID NO:1 might be combined with further substitutions as defined herein, i.e. substitutions on one or more position(s) corresponding to amino acid residue(s) 11, 281, 366, 442, 551, 554, 572, 624, 627, and/or 636 in the polypeptide according to SEQ ID NO:1 and as described herein. Using a cholesterol-producing yeast carrying such modified enzymes, in particular enzymes according to SEQ ID NO:1 comprising one of said amino acid substitution(s) as defined above, enzyme specificity could be increased in the range of at least about 2.2-times compared to using a non-modified yeast as defined herein in the range of at least about can be achieved.

In one embodiment, the modified enzyme as defined herein, in particular modified ARE2 and/or ARE1 activity, comprises an amino acid substitution at a position corresponding to residue 627 in the polypeptide according to SEQ ID NO:1, preferably substitution of glycine by aspartic acid (G627D), which corresponds to substitution of G595D in the polypeptide according to SEQ ID NO:3. The described amino acid substitution at a position corresponding to residue G627D in SEQ ID NO:1 might be combined with further substitutions as defined herein, i.e. substitutions on one or more position(s) corresponding to amino acid residue(s) 11, 281, 366, 442, 551, 554, 572, 624, 626, and/or 636 in the polypeptide according to SEQ ID NO:1 and as described herein. Using a cholesterol-producing yeast carrying such modified enzymes, in particular enzymes according to SEQ ID NO:1 comprising one of said amino acid substitution(s) as defined above, enzyme specificity could be increased in the range of at least about 2.2-times compared to using a non-modified yeast as defined herein.

In one embodiment, the modified enzyme as defined herein, in particular modified ARE2 and/or ARE1 activity, comprises an amino acid substitution at a position corresponding to residue 636 in the polypeptide according to SEQ ID NO:1, preferably substitution of cystine by serine (C636S). The described amino acid substitution at a position corresponding to residue C636S in SEQ ID NO:1 might be combined with further substitutions as defined herein, i.e. substitutions on one or more position(s) corresponding to amino acid residue(s) 11, 281, 366, 442, 551, 554, 572, 624, 626, and/or 627 in the polypeptide according to SEQ ID NO:1 and as described herein. Using a cholesterol-producing yeast carrying such modified enzymes, in particular enzymes according to SEQ ID NO:1 comprising one of said amino acid substitution(s), enzyme specificity could be increased in the range of at least about 3-times compared to using a non-modified yeast as defined herein.

A modified sterol acyltransferase according to the present invention, such as e.g. ARE2 and/or ARE1, preferably comprises at least one amino acid substitution on a position corresponding to F624L in the polypeptide according to SEQ ID NO:1, leading to an enzyme specificity of about 4. This could be increased by the introduction of one or more further amino acid substitution(s), e.g. amino acid substitution on a position corresponding to F572L and/or H554Q, leading to an increase of enzyme specificity in the range of more than 12-times compared to using a non-modified yeast as defined herein.

A modified sterol acyltransferase according to another embodiment of the present invention, such as e.g. ARE2 and/or ARE1, preferably comprises at least one amino acid substitution on a position corresponding to G627D in the polypeptide according to SEQ ID NO:1, leading to an enzyme specificity of more than 4. This could be increased by the introduction of one or more further amino acid substitution(s), e.g. amino acid substitution on a position corresponding to F572L and/or H554Q, leading to enzyme specificity increase of about 5-times compared to using a non-modified yeast as defined herein.

As used herein, the activity of ARE2 and/or ARE1 is modified. This might be achieved by, e.g. introducing (a) mutation(s) into the endogenous gene(s) coding for ARE2 and/or ARE1, i.e. amino acid substitution(s) on one or more positions as described herein. The skilled person knows how to genetically manipulate a yeast cell resulting in modification of ARE2 and/or ARE1 activity. These genetic manipulations include, but are not limited to, e.g. gene replacement, gene amplification, gene disruption, transfection, transformation using plasmids, viruses, or other vectors.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

The present invention is particularly directed to the use of such modified ARE2 and/or ARE1 enzymes as defined herein in a process for production of 7-DHC, an intermediate for vitamin D3. Preferably, the modified enzymes of the present invention are introduced and/or expressed in a suitable host cell, such as yeast, preferably sterol-producing yeast, in particular cholesterol-producing yeast cell, such as selected from *Saccharomyces cerevisiae*, *Schizosaccharomyces* spp., *Pichia* spp., *Klyuveromyces* spp., *Hansenula* spp. or *Yarrowia lipolytica*, preferably *S. cerevisiae*. The modified host is used for production of 7-DHC, which might be further converted into vitamin D3 and/or 25-hydroxyvitamin D3. A suitable host cell might be further modified to further increase production of 7-DHC, an important intermediate towards biosynthesis of vitamin D3, and/or reduce accumulation of side-products.

Thus, in one embodiment the invention is directed to a yeast strain having modified ARE2 and/or ARE1 activity and furthermore wherein ERG5 and ERG6 are inactivated. The yeast cell might be further modified via expression of a heterologous enzyme having C24-reductase activity, particularly selected from EC 1.3.1.72, such as a heterologous C24-reductase that is active on cholesta-7,24-dienol, zymosterol, or trienol (e.g. cholesta-5,7,25-trienol), preferably a plant or vertebrate sterol Δ24-reductase, more preferably from vertebrate source, even more preferably from human, pig, dog, mouse, rat, horse, *Danio rerio* or any known source, as long as it can be expressed within said yeast cell. Most preferably, the sterol Δ24-reductase is selected from *Danio rerio*, rat or human. The sequences expressing said sterol Δ24-reductase enzymes are publicly available, including but not limited to UniProtKB/Swiss-Prot reference Q15392, Q6OHC5, Q8VCH6, Q5BQE6, Q39085 or P93472 (see e.g. WO2003064650).

In another embodiment, the host cell according to the present invention might be further modified via introduction of homologs of endogenous enzymes involved in biosynthesis of 7-DHC, such as e.g. C5-sterol desaturase (ERG3) and/or C8-sterol isomerase (ERG2), resulting in increased specificity and/or productivity of 7-DHC with reduced accumulation of side-products or vitamin D3 intermediates, including but not limited to including zymosterol, lanosterol and/or lathosterol.

In a particular embodiment, the invention relates to a process for improving a host cell towards production of 7-DHC, wherein a modified host cell as defined herein, i.e. modified via introduction of one or more amino acid substitutions in sterol acyltransferases ARE2 and/or ARE1 as defined herein, in particular a cholesterol-producing yeast cell, preferably a yeast cell in which ERG5 and ERG6 are inactivated and wherein optionally a heterologous enzyme having C-24-reductase activity as defined herein is expressed, and/or wherein optionally homologs of endogenous ERG2 and/or ERG3 are expressed, wherein the host cell is improved such that the percentage of 7-DHC, in the total amount of sterol produced by said host cell is increased and/or the activity of the host cell towards production of sterols is increased, compared to a non-modified host cell as defined herein.

In one embodiment, the present invention is directed to modified sterol acyltransferases, particularly modified ARE2 and/or ARE1, comprising at least one or more amino acid substitution(s) as defined herein, wherein the specificity of the enzyme is increased compared to the specificity of the non-modified enzymes, leading to higher ratio of 7-DHC to side-products including e.g. zymosterol in a sterol mix produced by a suitable host cell carrying such modified sterol acyltransferase. The ratio might be increased by at least about 1.4-times, such as e.g. via introduction of amino acid substitutions corresponding to H554Q in the respective ARE2 and/or ARE1 sequence, such as increased by at least 3, such as e.g. via introduction of amino acid substitutions corresponding to E11G-F624L, I442V-G627D, or I442V-F624L-L626F in the respective ARE2 and/or ARE1 sequence, such as increased by at least 4-times, such as e.g. via introduction of amino acid substitutions corresponding to F624L or G627D in the respective ARE2 and/or ARE1 sequence, such as at least 5, 10 or even 12-times or more, such as e.g. via introduction of amino acid substitutions corresponding to H554Q-F572L-G627D or E11G-D366V-I442V-G627D-C636S in the respective ARE2 and/or ARE1 sequence.

In one embodiment, the present invention is directed to modified sterol acyltransferases, particularly modified ARE2 and/or ARE1, comprising at least one or more amino acid substitution(s) as defined herein, wherein the activity of the enzyme is increased compared to the activity of the non-modified enzymes, leading to higher overall production of sterols and/or steryl esters, including higher amounts of 7-DHC produced by a suitable host cell carrying such modified sterol acyltransferase. Thus, the relative ester formation, i.e. ratio of all esters to free 7-DHC might be increased by at least 1.2-times, such as e.g. via introduction of amino acid substitutions corresponding to H55Q or H554Q-F572L in the respective ARE2 and/or ARE1 sequence, such as increased by at least 2, or 3-times, such as e.g. via introduction of amino acid substitutions corresponding to I442V-G627D or I442V-L626F-G627D in the respective ARE2 and/or ARE1 sequence. The total 7-DHC production might be increased by at least about 1.2 to 1.4-times via introduction of one or more amino acid substitution(s) as described herein.

Using the modified host cell, e.g. yeast, such as a sterol-producing yeast, in particular a cholesterol-producing yeast, as described herein the percentage of 7-DHC in the sterol mix could by increased by at least 40%, such as 50, 60, 70, 80, 90% 7-DHC based on the total amount of sterols.

In one aspect of the present invention, a host cell comprising modified ARE2 and/or ARE1 activity as defined herein is used in a process for production of vitamin D3 precursor 7-DHC. The modified host cell may be cultured in an aqueous medium supplemented with appropriate nutrients under aerobic or anaerobic conditions and as known by the skilled person for the respective cholesterol-producing host cells. Optionally, such cultivation is in the presence of proteins and/or co-factors involved in transfer of electrons, as known in the art. The cultivation/growth of the host cell may be conducted in batch, fed-batch, semi-continuous or continuous mode. Depending on the host cell, preferably, production of vitamin D3 and precursors thereof such as 7-DHC can vary, as it is known to the skilled person. Cultivation and isolation of 7-DHC and other intermediates in production of vitamin D3 is described in e.g. WO2011067144 or WO2017108799. The 7-DHC might be isolated and/or optionally further purified from the sterol mix and might be further converted to vitamin D3 and/or 25-hydroxyvitamin D3 using methods known in the art.

The terms "ARE1" and "Are1p", "ARE2" and "Are2p", "ERG5" and "Erg5p", "ERG6" and "Erg6p" are used interchangeably herein and refer to a polypeptide encoded by the respective genes are1, are2, erg5, and erg6. For the purpose of the present invention, the cholesterol-producing yeast cell is modified such that it does show modified activity of ARE2 and/or ARE1, e.g. carries a modification in either endogenous ARE2, ARE1 or both, leading to modified specificity of ARE2 and/or ARE1, wherein said modification comprises the introduction of one or more amino acid substitution(s) as defined herein.

Genes encoding ERG5, ERG6, ARE1, ARE2, ERG2, ERG3, or sterol Δ24-reductase (ERG4), cultivation and genetic engineering of the yeast cell as used herein are known and described in e.g. U.S. Pat. No. 7,608,421.

As used herein, the terms "C-24-reductase" or "Δ24-reductase" are used interchangeably herein. In yeast, this enzyme is encoded by erg4 and is active on the methyl-group of the carbon atom on position 24. Trienol, which does not exhibit such methyl-group on said position, is therefore not an acceptable substrate for the yeast ERG4.

The terms "C-8 sterol isomerase", "delta 8,7-isomerase", or "enzyme having C-8 sterol isomerase" are used interchangeably herein and refer to enzymes which are capable of catalyzing the conversion of cholesta-8-enol into cholesta-7-enol and/or zymosterol into cholesta-7,24-dienol. In yeast, this enzyme is encoded by erg2. In yeast, this enzyme is encoded by erg2. A preferred ERG2 homolog to be used in a modified host cell according to the present invention is a polypeptide having at least 41%, such as e.g. at least 44, 45, 48, 49, 53, 56, 60, 70, 80, 90, 92, 95, 98 or up to 100% identity to SEQ ID NO:5 showing C-8 sterol isomerase activity and including polynucleotides encoding such polypeptide obtainable from *Ustilago maydis*. Particularly, 1 or more copies, such as at least 1, 2, 3, 5, of said ERG2 homolog are expressed in a modified host cell as defined herein.

The terms "C-5 sterol desaturase", "enzyme having C-5 sterol desaturase", "desaturase" or "ERG3-homolog" are used interchangeably herein and refer to enzymes which are capable of catalyzing the conversion of cholesta-8-enol into cholesta-7,24-dienol and/or cholesta-7-enol into cholesta-5, 7,24-trienol and/or 7-DHC. In yeast, this enzyme is encoded by erg3. A preferred ERG3 homolog to be used in a modified host cell according to the present invention is a polypeptide having at least 45%, such as e.g. at least 50, 52, 60, 70, 80, 90, 92, 95, 98 or up to 100% identity to SEQ ID NO:7 showing C-5 sterol desaturase activity and including polynucleotides encoding such polynucleotide obtainable from *Pichia pastoris* or *Schizosaccharomyces pombe*. Particularly, 1 or more copies, such as at least 1, 2, 3, 5, of said ERG3 homolog are expressed in a modified host cell as defined herein.

The "relative ester formation" as defined herein is the ratio (all ester/free 7-DHC)$_{mutant}$/(all ester/free 7-DHC)$_{wt}$. Enzyme "specificity" as defined herein is the ratio (7-DHC ester/zymosterol ester)$_{mutant}$/(7-DHC ester/zymosterol ester)$_{wt}$. The "total 7-DHC production" as defined herein is the ratio (total 7-DHC)$_{mutant}$/(7-DHC)$_{wt}$.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity, such as e.g. by HPLC.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code).

In particular, the present invention features the present embodiments:

(1) A modified enzyme as defined herein with sterol acyltransferase activity having sterol acyltransferase activity comprising one of more amino acid substitution(s) at (a) position(s) corresponding to residues selected from the group consisting of 11, 281, 366, 442, 551, 554, 572, 624, 626, 627, 636, and combinations thereof in the polypeptide according to SEQ ID NO:1, preferably one or more amino acid substitution(s) corresponding to E11G and/or L281I and/or D366V and/or I442V and/or H551Y and/or H554Q and/or F572L and/or F624L and/or L626F and/or G627D and/or C636S and/or combinations thereof.

(2) The modified enzyme as defined herein and of embodiment (1) catalyzing the esterification of sterols comprising 7-dehydrocholesterol and zymosterol, wherein the ratio of 7-DHC to zymosterol in the sterol esters is increased by at least about 1.4-times compared to the ratio of 7-DHC to zymosterol in the catalysis using the respective non-modified enzyme.

(3) The modified enzyme as defined herein and of embodiment (1) or (2), wherein the amino acid substitution(s) is/are selected from F624L, G627D, E11G, H554Q, I442V and combinations thereof.

(4) A host cell, preferably a yeast, more preferably a sterol-producing yeast, even more preferably a cholesterol-producing yeast, comprising a modified enzyme as defined herein and according to any of embodiments (1), (2), (3), said host cell optionally further comprising one of more amino acid substitution(s) at (a) position(s) corresponding to residues selected from 592 and/or 595 in the polypeptide according to SEQ ID NO:3, preferably substitution corresponding to F592L and/or G595D.

(5) The host cell as defined herein and of embodiment (4) used for production of a sterol mix comprising 7-DHC and zymosterol, wherein the ratio of 7-DHC to zymosterol is increased by at least about 1.4-times compared to a host cell wherein expressing a non-modified enzyme.

(6) The host cell as defined herein and of embodiment (4) or (5), which optionally further comprises:

inactivation of ERG5 and ERG6 and/or expression a heterologous enzyme selected from EC 1.3.1.72 having sterol Δ24-reductase activity, preferably wherein the heterologous enzyme is originated from plant or vertebrate, more preferably originated from human, pig, dog, mouse, rat, horse or *Danio rerio*.

(7) A process for reducing the percentage of zymosterol in a sterol mix comprising zymosterol and 7-DHC comprising cultivating a host cell as defined herein and of one of the embodiments (4), (5) or (6) under suitable conditions and optionally isolating and/or purifying the 7-DHC from the sterol mix or a process for increasing the percentage of 7-DHC in a sterol mix comprising 7-DHC and zymosterol comprising cultivating a host cell as defined herein and of one of the embodiments (4), (5) or (6) under suitable conditions and optionally isolating and/or purifying the 7-DHC from the sterol mix.

(8) A process for production of 7-DHC comprising enzymatic conversion of acetyl-CoA into a sterol mix comprising zymosterol and 7-DHC with a host as defined herein and of one of the embodiments (4), (5) or (6), wherein the percentage of 7-DHC in the sterol mix is at least 40%, with optionally further conversion of 7-DHC into vitamin D3 and/or 25-hydroxyvitamin D3.

(9) Use of a modified enzyme as defined herein and of any of embodiments (1), (2), (3) or a host cell as defined herein and of one of the embodiments (4), (5) or (6) in a process for production of 7-DHC, wherein the 7-DHC is isolated from a sterol mix comprising zymosterol and 7-DHC, and wherein the ratio of 7-DHC to zymosterol is increased by at least about 1.4-times compared to a process using the respective non-modified enzyme and host cell, respectively.

FIGURES

FIG. 1. HPLC analysis of lipid extracts of ARE2 wild-type strain ("WT") and Are2 variants #2 and #1 (see Table 1). With regards to esters of 7-DHC ("7-DHC ester") and esters of zymosterol ("Zym ester") two ester forms were detected as indicated by dark and light grey in the respective columns, free 7-DHC is indicated in black. (A) ratio of 7-DHC to ester formation, (B) ratio of total 7-DHC (including free and ester forms) to total zymosterol esters, (C) formation of free 7-DHC, 7-DHC esters and zymosterol esters shown by different columns. Strains were cultivated for two days with two glucose feedings in flasks without baffles. Data are mean values of 3 independent transformants each cultivated once.

Figure 2:
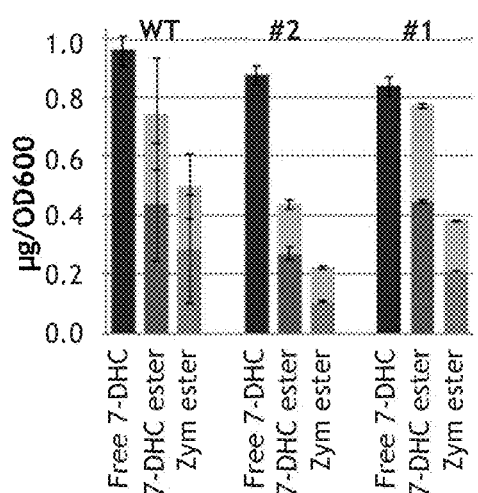
Figure 2:
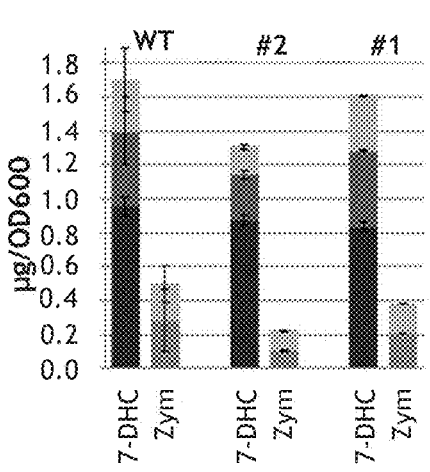
Figure 2:
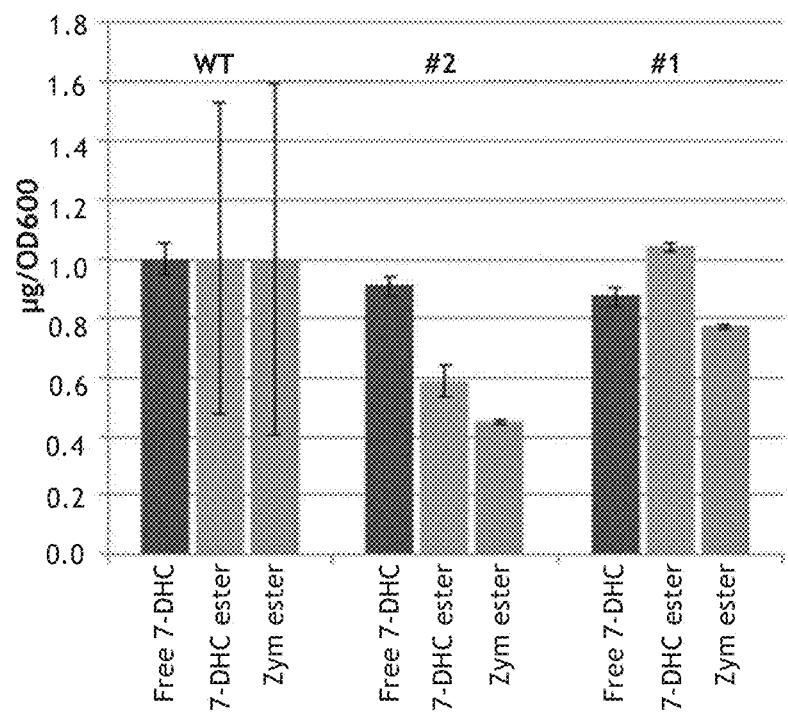

FIG. 2. HPLC analysis of lipid extracts of ARE2 wild-type strain ("WT") and Are2 variants #2 and #1 (see Table 1). For further details see legend to FIG. 1. Strains were cultivated for four days with one glucose feeding in flasks without baffles. Data are mean values of 2 independent transformants each cultivated once.

Figure 3:
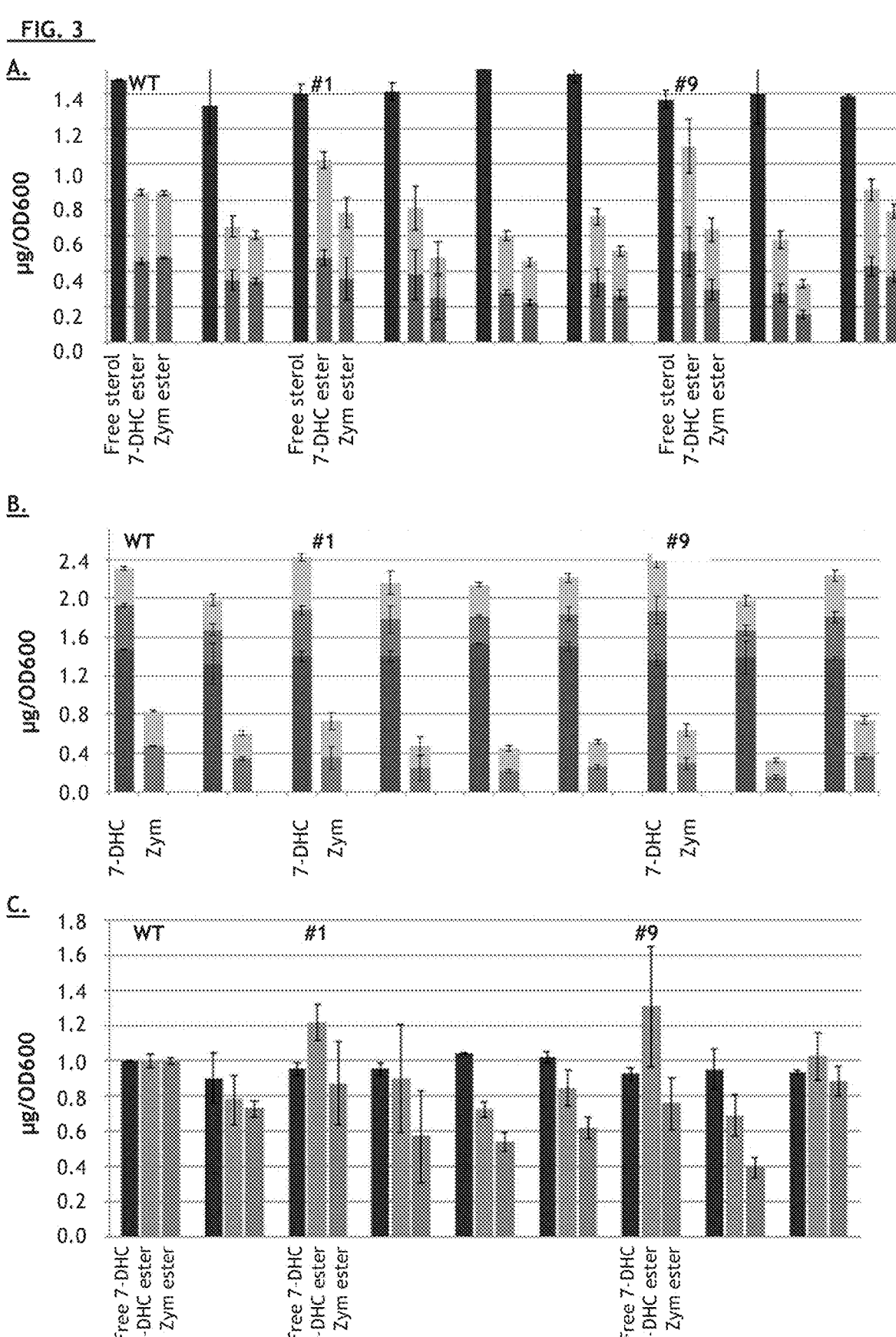

FIG. 3. HPLC analysis of lipid extracts of ARE2 wild-type strain ("WT") and Are2 variants #9 and #1 (see Table 1). For further details see legend to FIG. 1. HPLC analysis according to standard procedure. For further details see text.

Figure 4:
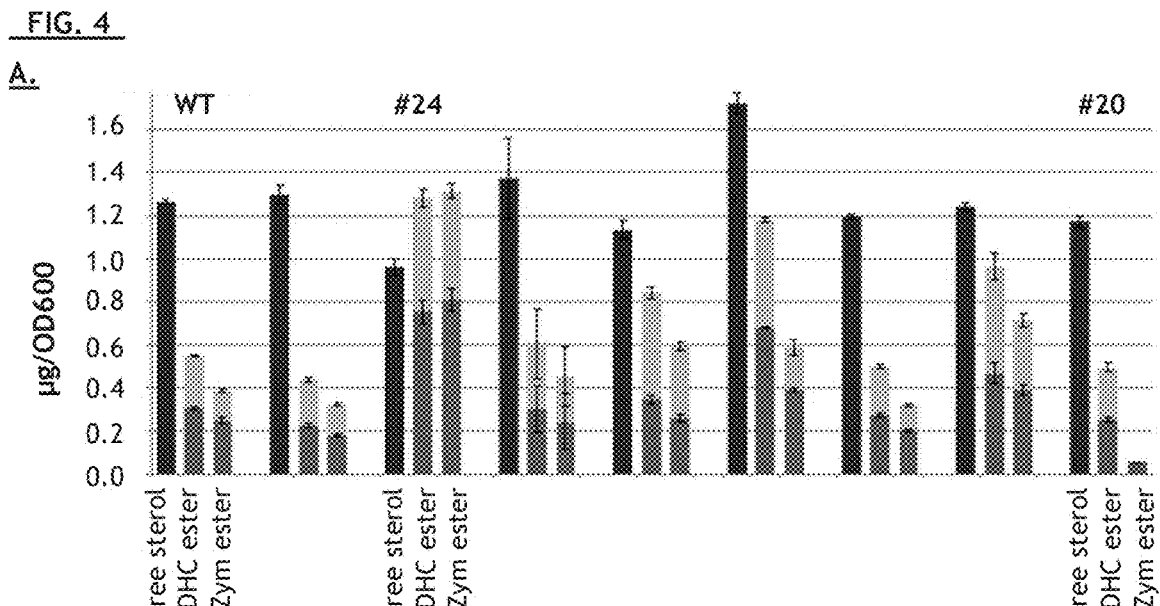
Figure 4:
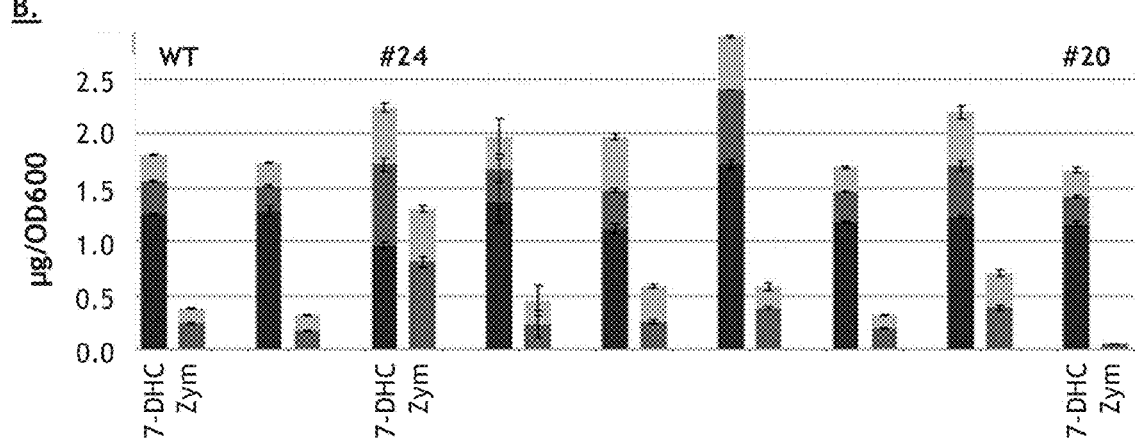
Figure 4:
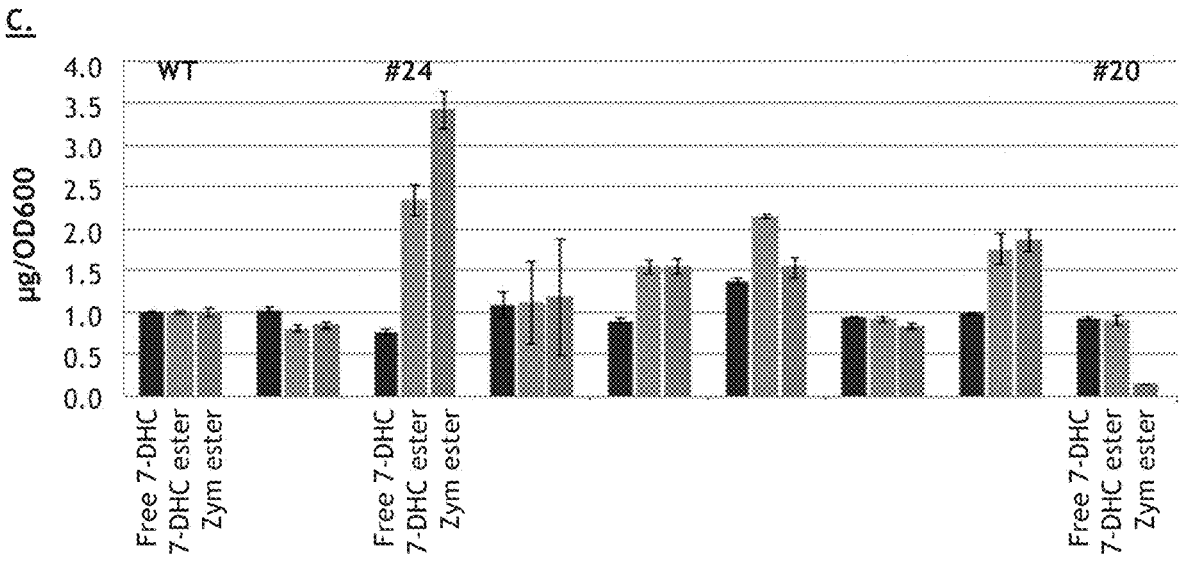

FIG. 4. HPLC analysis of lipid extracts of ARE2 wild-type strain ("WT") and Are2 variants #24 and #20 (see Table 1). For further details see legend to FIG. 1. HPLC analysis according to standard procedure. For further details see text.

Figure 5:
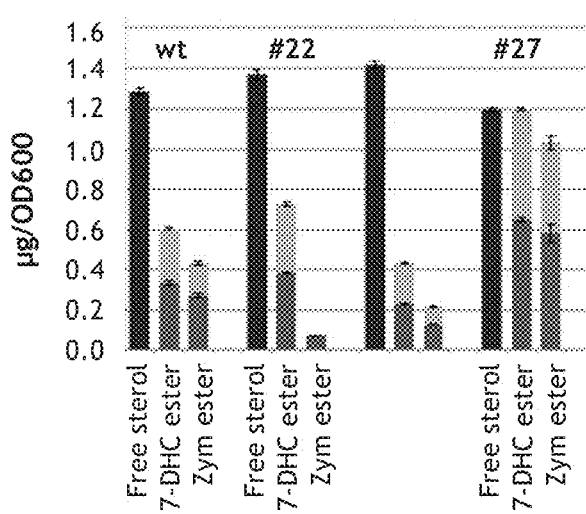
Figure 5:
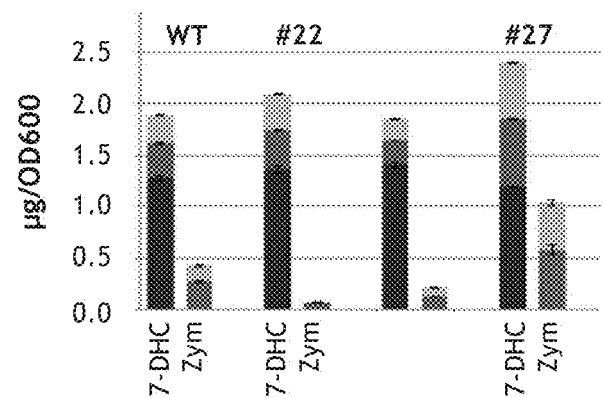
Figure 5:
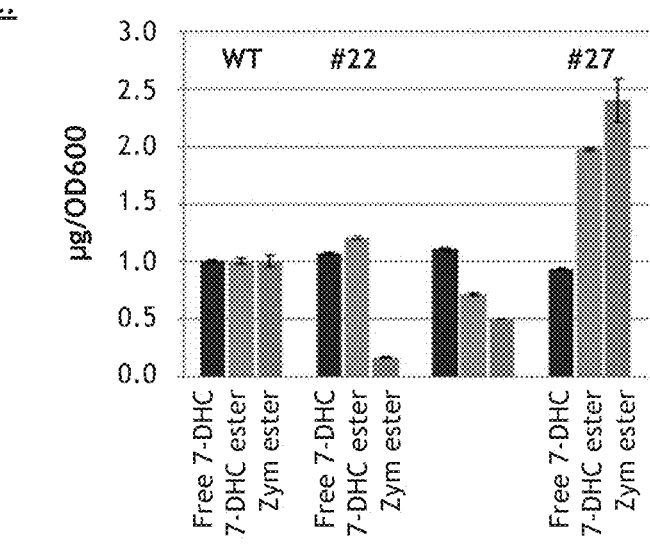

FIG. 5. HPLC analysis of lipid extracts of ARE2 wild-type strain ("WT") and Are2 variants #22 and #27 (see Table 1). For further details see legend to FIG. 1. HPLC analysis according to standard procedure. For further details see text.

Figure 6:
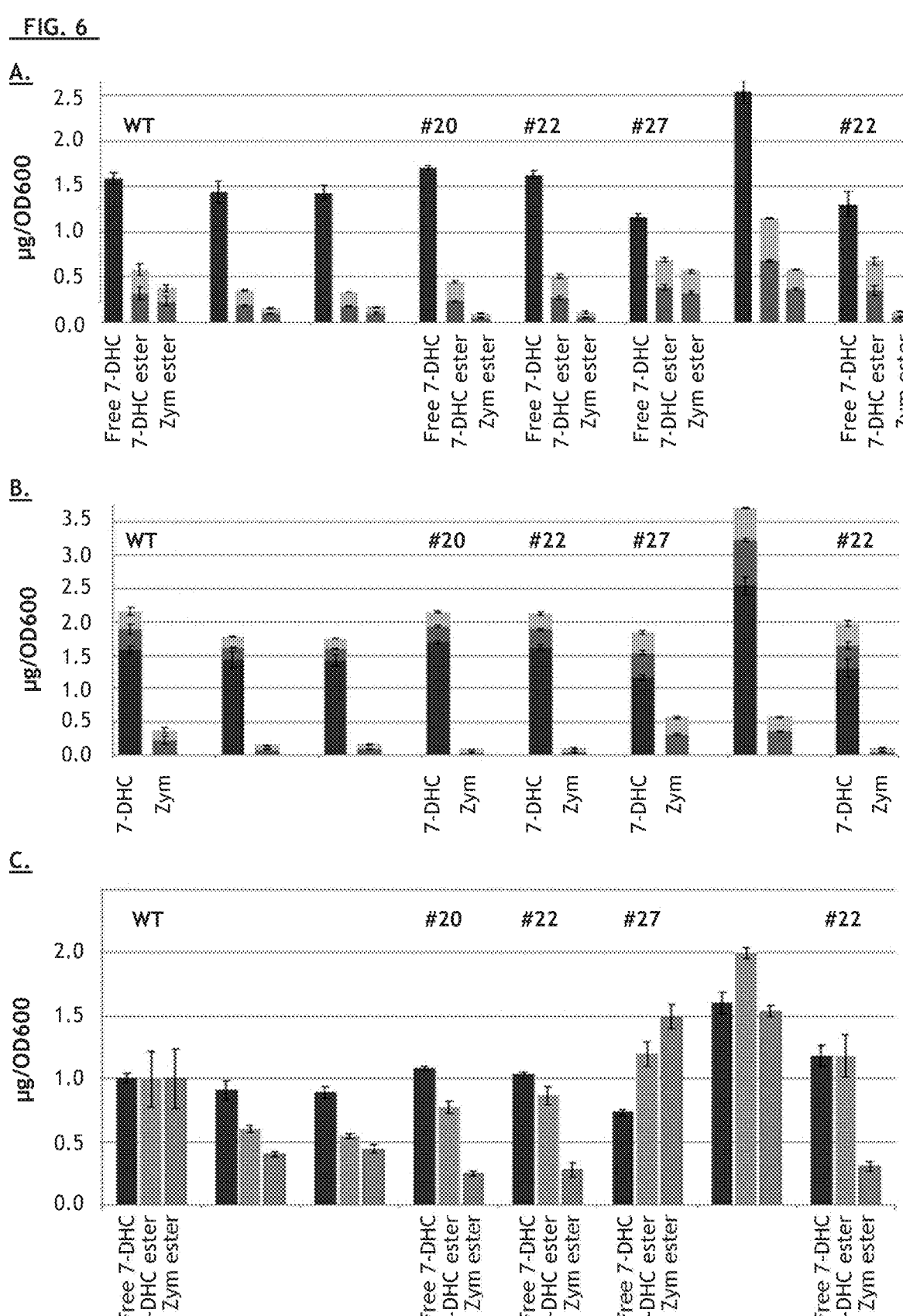

FIG. 6. HPLC analysis of lipid extracts of ARE2 wild-type strain ("WT") and Are2 variants #20, #22, #27 and #22 (see Table 1). For further details see legend to FIG. 1. HPLC analysis according to standard procedure. For further details see text.

Figure 7:
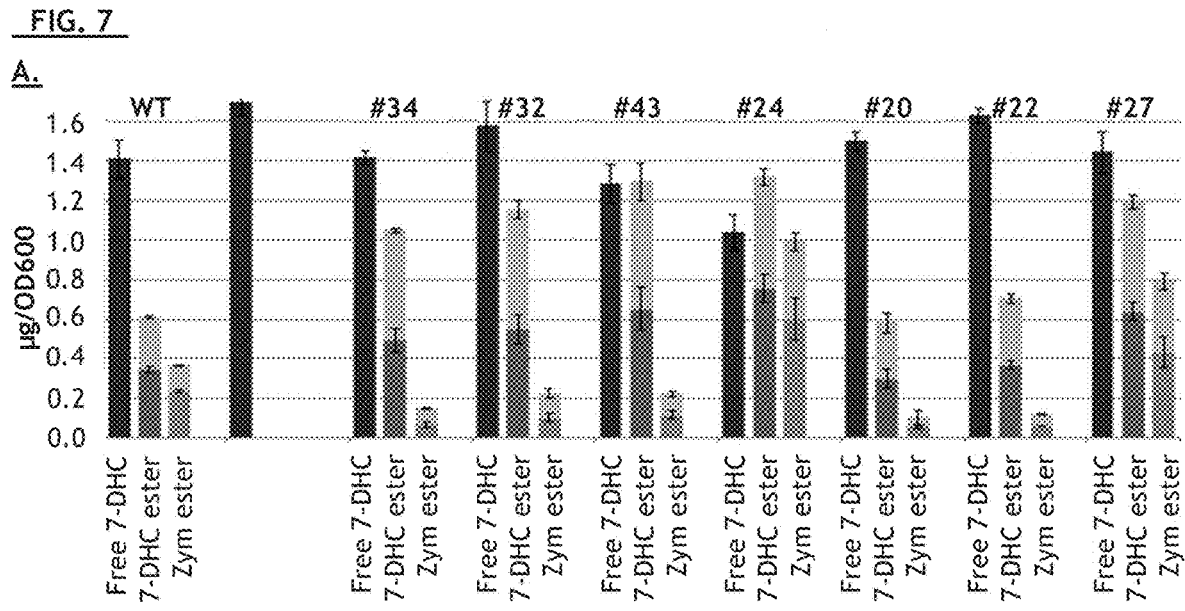
Figure 7:
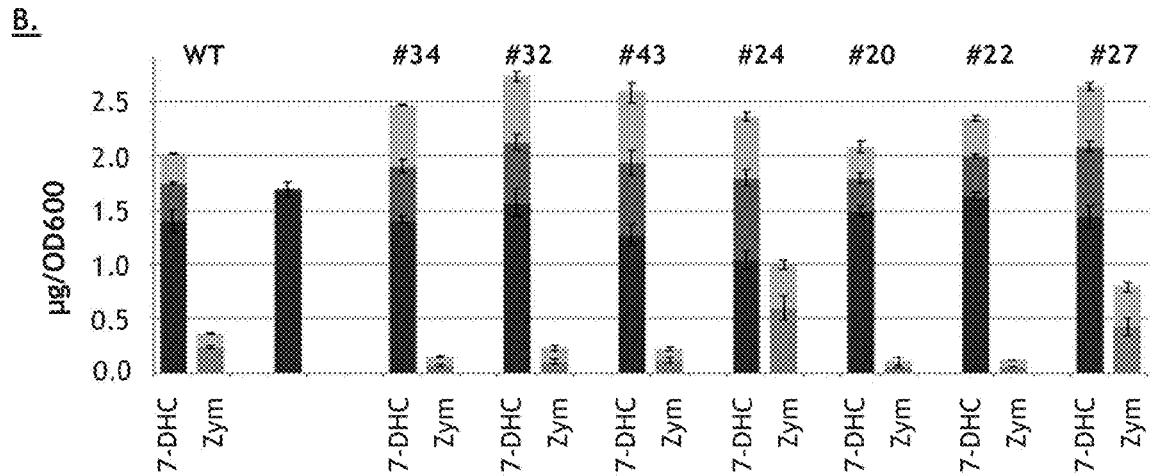
Figure 7:
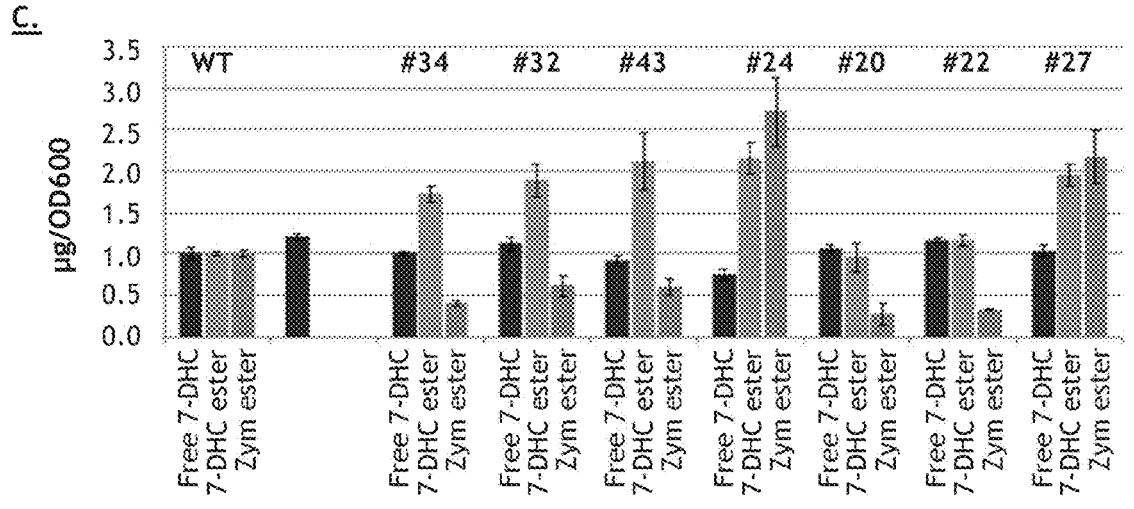

FIG. 7. HPLC analysis of lipid extracts of ARE2 wild-type strain ("WT") and Are2 variants #34, #32, #43, #24, #20, #22, and #27 (see Table 1). For further details see legend to FIG. 1. HPLC analysis according to standard procedure. For further details see text.

Figure 8:
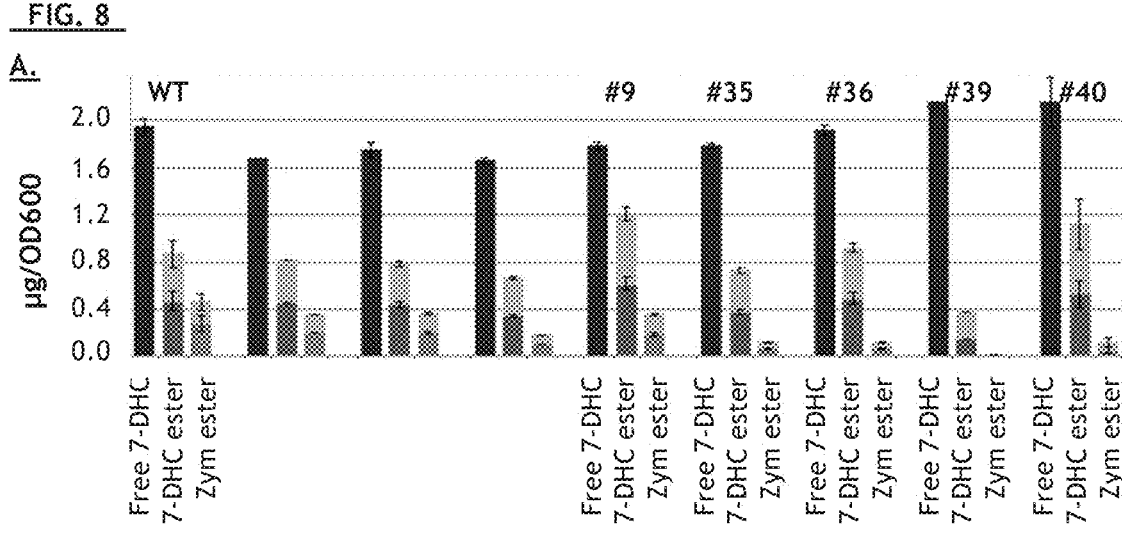
Figure 8:
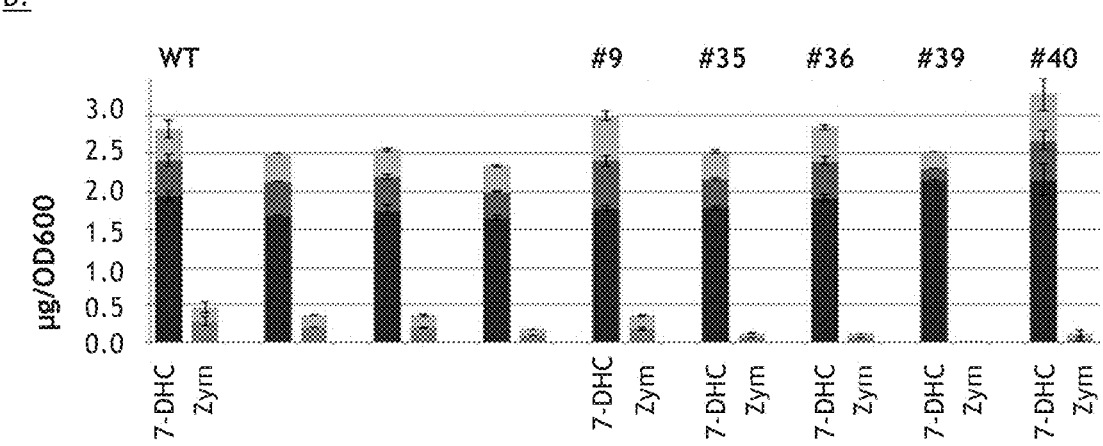
Figure 8:
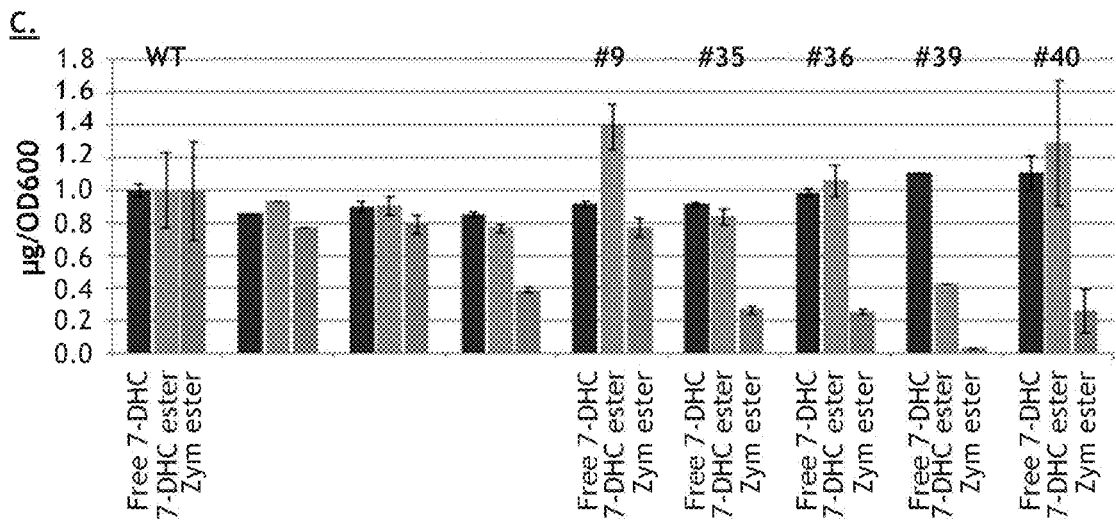

FIG. 8. HPLC analysis of lipid extracts of ARE2 wild-type strain ("WT") and Are2 variants #9, #35, #36, #39, and #40 (see Table 1). For further details see legend to FIG. 1. HPLC analysis according to standard procedure. For further details see text.

Figure 9:
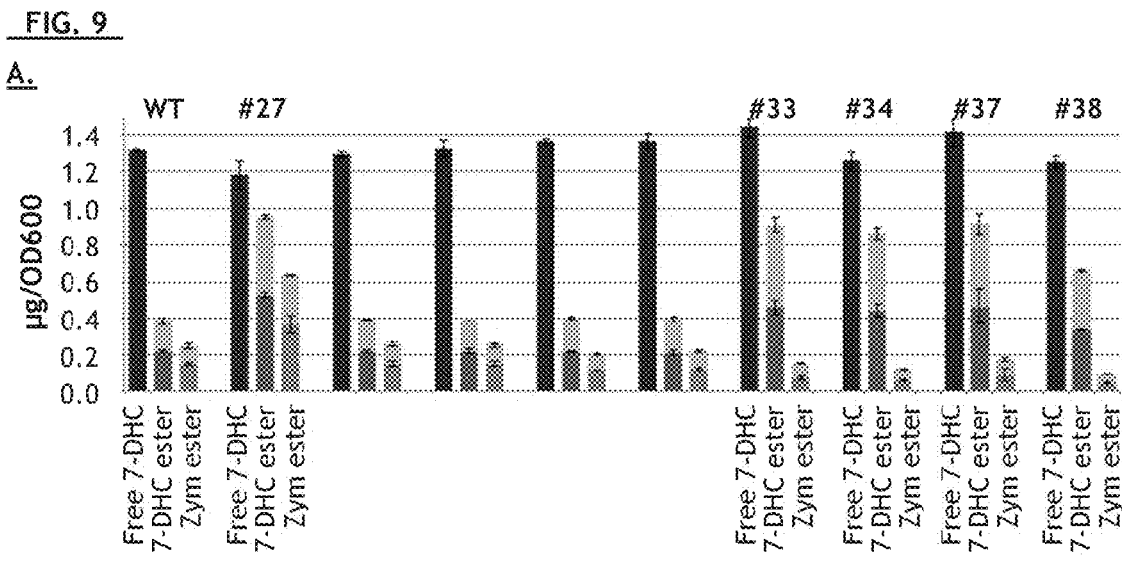
Figure 9:
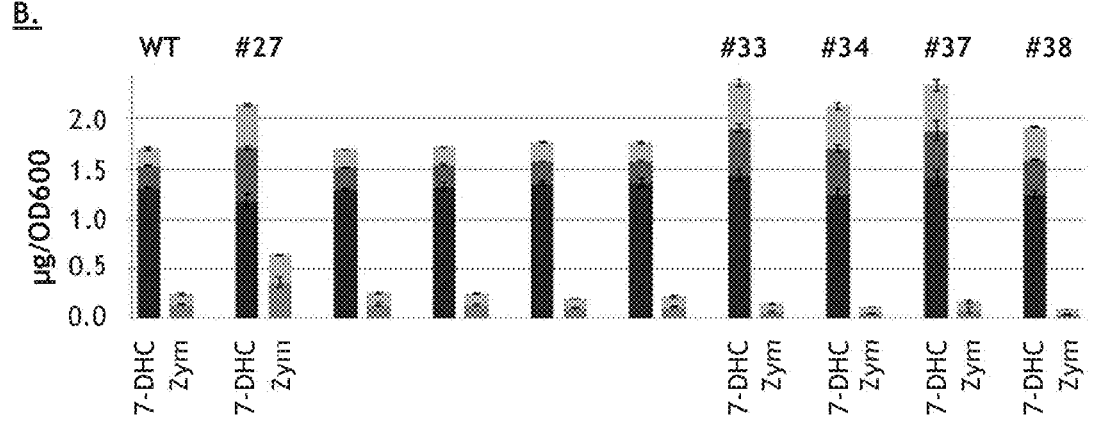
Figure 9:
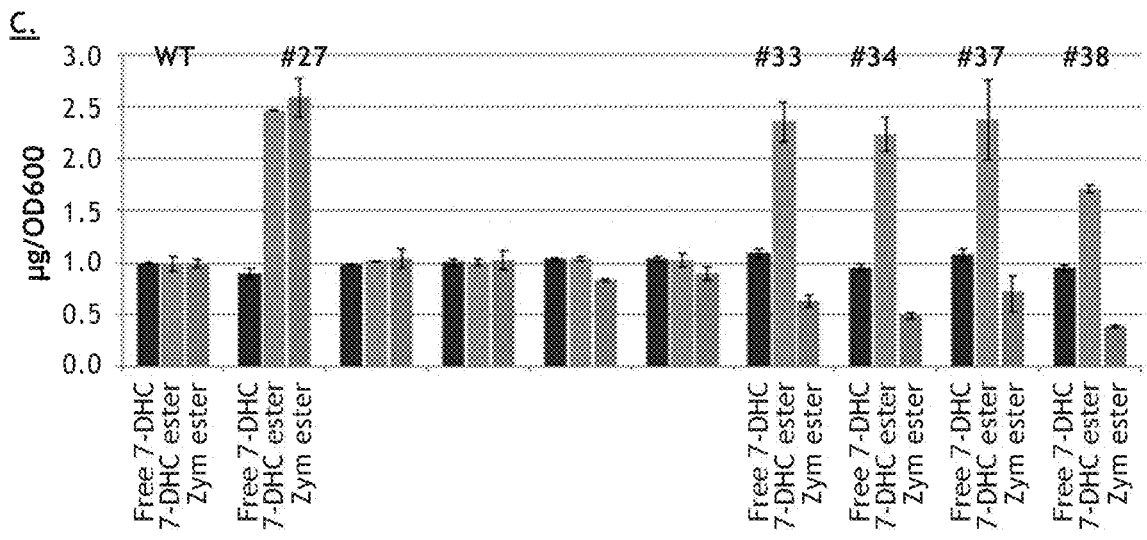

FIG. 9. HPLC analysis of lipid extracts of ARE2 wild-type strain ("WT") and Are2 variants #27, #33, #34, #37, and #38 (see Table 1). For further details see legend to FIG. 1. HPLC analysis according to standard procedure. For further details see text.

Figure 10:
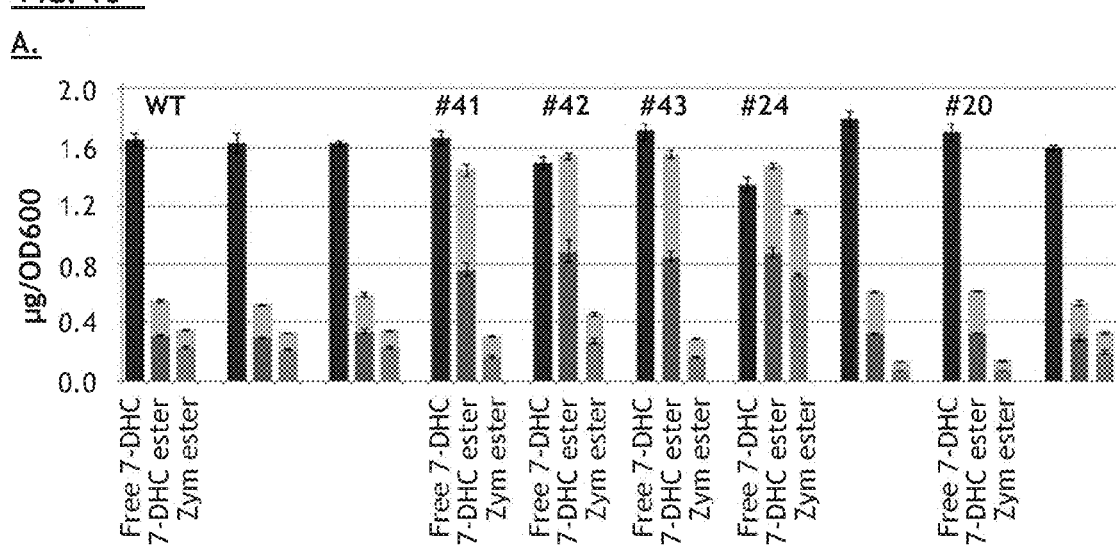
Figure 10:
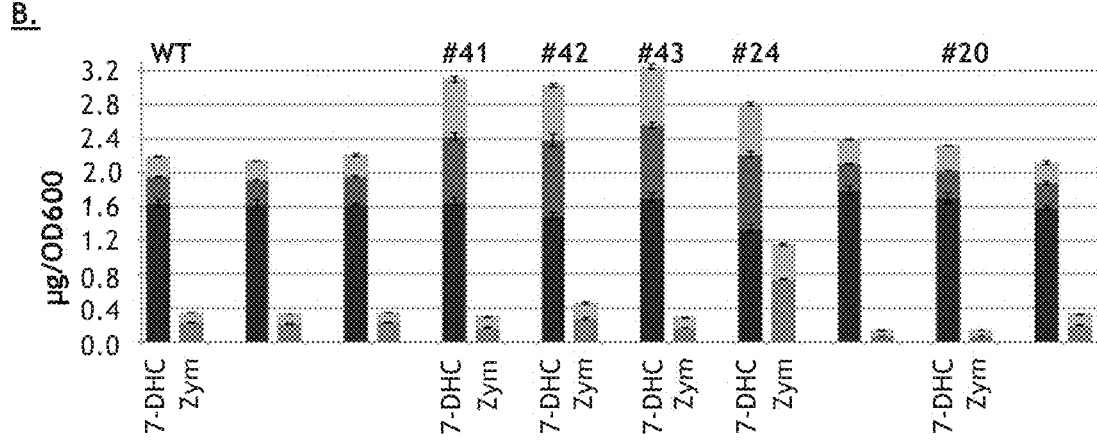
Figure 10:
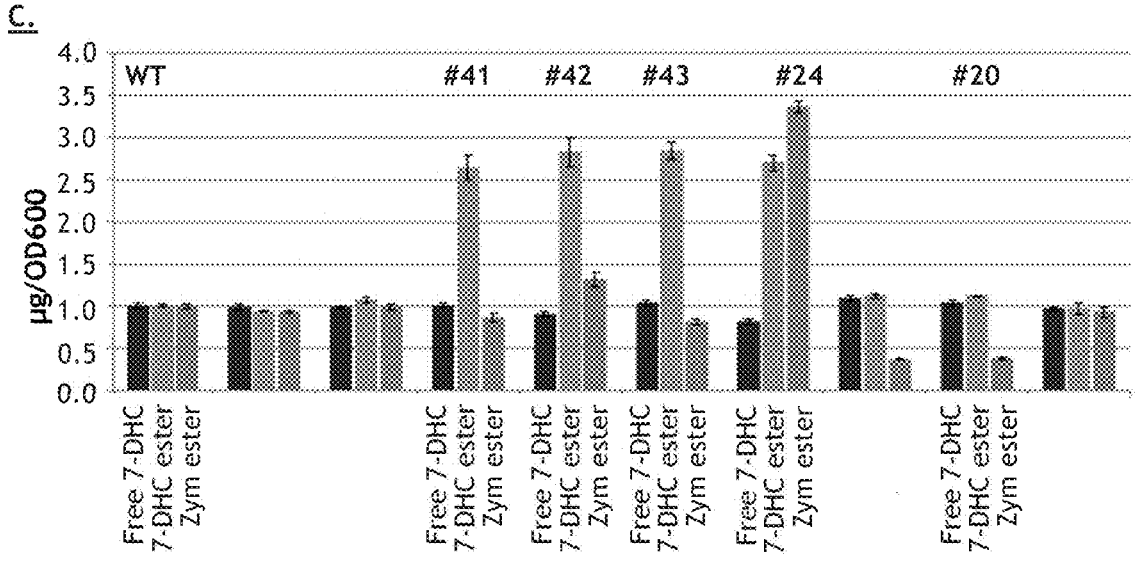

FIG. 10. HPLC analysis of lipid extracts of ARE2 wild-type strain ("WT") and Are2 variants #41, #42, #43, #24, and #20 (see Table 1). For further details see legend to FIG. 1. HPLC analysis according to standard procedure. For further details see text.

The following examples are illustrative only and are not intended to limit the scope of the invention in any way.

EXAMPLES

Example 1: Generation and Screening of ARE2 Mutants

An error prone library of 10,000 yeast clones expressing variants of *Saccharomyces cerevisiae* acyltransferase 2 (ScAre2) were screened by thin layer chromatography (TLC) for improved 7-DHC content in sterol ester fraction (for wild-type sequences of ARE1 and ARE2 (see sequence listing). The screening method comprises the simultaneous extraction and separation of sterols from cells with slightly digested cell walls. The treated biomass was directly applied on the TLC plate and immersed into the solvent, which did the extraction and separation of sterol containing fractions in one step. In the sterol ester fraction the ratio of sterols with conjugated double bonds (as e.g. 7-DHC) was set into relation to sterols without conjugated double bonds by exploiting the different spectrophotometric properties of the compounds with the conjugated double bonds (e.g. ability to quench fluorescence, UV detection).

The best variants were re-screened in quintuplicates, sequenced, cultivated in shake flasks and analyzed in biological triplicates by HPLC-UV to determine the sterol and sterol ester compositions.

Plasmids containing the best variants were isolated and re-transformed into a cholesta-5,7,24-trienol producing *Saccharomyces cerevisiae* strain 10A (are1 are2 erg5 erg6::24R; for construction see Example 1 in WO2017108799). Mutations of variants with multiple amino acid exchanges were separated by introducing respective mutation into ARE2 by site-directed mutagenesis (silent mutations were not taken into account) to find out which mutation caused the desired effect. Strains were cultivated and analyzed by HPLC.

Example 2: HPLC-UV Analysis Standard Procedure

Pre-cultures—10 ml YPD with geneticin (100 µg/mL)—were inoculated with our strains of interest (3 transformants per Are2 variants) and grown at 30° C. to appropriate density (24 to 48 h). For better comparison, three different transformants with the wild-type ARE2 plasmid were also inoculated, which were transformed at the same time as the variants. Main cultures of 50 mL YPD with geneticin were inoculated to $OD_{600}$ 0.1 in 250 mL shake flasks without baffles and were cultivated for 3 days with 3 times glucose feeding (glucose was added to 2% final concentration after approx. 30, 45, and 60 h) with 200 rpm and 80% humidity at 30° C. 200 OD units of biomass were harvested (centrifuged for 5 min with 1600×g and supernatant was removed) in 15 mL Greiner tubes and stored at −20° C. until analysis.

For extraction, the 200 OD cell pellet was thawed, resuspended in 1 mL zymolyase solution (5 mg/mL zymolyase 20T in 50 mM KPi, pH 7, with 1 M D-sorbitol) and incubated for 15 min at 37° C. (750 rpm on thermomixer). The zymolyase solution was removed after centrifugation (2500×g, 5 min) and 3.73 mL of absolute EtOH were added to the pellet (resuspended with 1 mL by pipetting up and down carefully, then adding additional 2.73 mL). 267 µL of internal standard (cholesteryl acetate, 1 mg/mL in EtOH) were added, the cell suspension was vortexed and heated to 70° C. for 1 h with mixing (750 rpm on thermomixer). After some minutes of leaving the tubes to cool down to room temperature, the cell debris was pelleted (2500×g, 10 min at room temperature) and 3 mL of the supernatant were transferred into Pyrex tubes which were brought to dryness under N2. The lipids were taken up in 200 µL of ethyl acetate (vortexed and mixed with 750 rpm on a thermomixer at 40° C. for 15 min). The solution was centrifuged once more (2500×g, 5 min) and transferred into a glass vial with inlay for the subsequent HPLC-UV analysis.

Lipid extracts were analyzed by HPLC with UV detection at two wavelengths (210 nm and 280 nm). Zymosterol compounds were detected at 210 nm, 7-DHC compounds were quantified at 280 nm.

Solvent: 80% EtOH 20% MeOH 0.1% TFA
Column: YMC-Pack Pro C18 RS
Method: injection volume: 10 µL
    injector thermostat: 40° C.
    flow: 0.6 mL/min
    column thermostat: 20° C.
    UV detection: 210 nm, 280 nm (sterols with conjugated double bonds)
Standard mixtures of 7-DHC, zymosterol, cholesteryl acetate and squalene in 3 different concentrations (0.5, 1.0, and 2.0 mg/mL of each substance) were analyzed as well and standard curves were generated for each substance to calculate the concentration in µg/µL sterol in extract or µg/$OD_{600}$.

Example 3: Evaluation of ARE2 Variants with Regards to Activity and/or Specificity For direct comparison, the wild-type ARE2 plasmid was re-transformed along with the plasmids expressing Are2 variants (see Ex. 1) into strain 10A and the resulting strains were analyzed (see Ex. 2) in the same run. The results of the HPLC analyses are summarized in Table 1 and FIGS. 1-10. Values in the table give the fold change between strains expressing the mutant/variant compared to the wild type. The first value indicates improvements regarding the ratio between the ester fraction and the free 7-DHC fraction while the second value shows the improvement concerning the ratio of 7-DHC and zymosterol in the ester fractions. The third value is a comparison of total 7-DHC content in biomass of mutants and wild type. Some of the listed variants showed especially improvement in the ester level while others showed improvements in the 7-DHC/zymosterol ratio in the ester fraction.

TABLE 1A

Summary of relative ester formation of Are2 variants based on several independent experiments. "Relative ester formation" means the x-times increase in the percentage of 7-DHC based on the total amount of sterols generated using the indicated amino acids exchange instead of a wild-type ARE2.; "7-DHC-ester/zym-ester" means ratio of esters from 7-DHC towards esters of zymosterol ("zym"); "7-DHC-total/zym-total" is the ratio of total 7-DHC (free and esters) towards total zymosterol (free and esters). For more explanation, see text.

| # | AA exchange(s) | Relative ester formation | 7-DHC-ester/ zym-ester | 7-DHC-total/ zym-total |
|---|---|---|---|---|
| 1 | H554Q | 1.2 | 1.0-2.0 | 3.0-4.2 |
| 9 | H554Q-F572L | 1.2 | 1.7-3.4 | 3.9-8.5 |
| 15 | L281I | 1.5 | | |
| 24 | I442V-L626F | 3.5 | 1.0-1.3 | 1.7-2.4 |
| 27 | E11G-D366V-C636S | 2.2 | 1.2-1.5 | 2.3-3.4 |
| 32 | E11G-D366V-F624L-C636S | 1.3 | 5.3 | 12.7 |
| 33 | E11G-D366V-F624L-C636S | 1.5 | 6.0 | 15.4 |
| 34 | E11G-D366V-G627D-C636S | 1.4 | 7.1-7.3 | 16.417.8 |
| 37 | E11G-D366V-I442V-F624L-C636S | 1.6 | 5.4 | 13.9 |
| 38 | E11G-D366V-I442V-G627D-C636S | 1.3 | 7.1 | 20.5 |
| 41 | I442V-F624L-L626F | 1.9 | 4.8 | 10.4 |
| 42 | I442V-L626F-G627D | 2.5 | 3.4 | 6.7 |
| 43 | I442V-G627D | 1.9 | 5.5-5.9 | 11.76-11.7 |

TABLE 1B

Summary of specificity of Are2 variants based on several independent experiments. The number indicates the x-times increase in the percentage of 7-DHC compared to the percentage of zymosterol in the sterol mx generated using the indicated amino acids exchange instead of a wild-type ARE2. For more explanation, see text.

| # | AA exchange(s) | Specificity |
|---|---|---|
| 1 | H554Q | 1.4 |
| 2 | V286V-H551Y-F572L-S633S | 1.7 |
| 9 | H554Q-F572L | 1.8 |
| 20 | F624L | 3.9 |
| 22 | G627D | 4.4 |
| 32 | E11G-D366V-F624L-C636S | 3.1 |
| 33 | E11G-D366V-F624L-C636S | 3.8 |
| 34 | E11G-D366V-G627D-C636S | 4.4 |
| 35 | E11G-F624L | 3.2 |
| 36 | E11G-G627D | 4.2 |
| 37 | E11G-D366V-I442V-F624L-C636S | 3.4 |
| 38 | E11G-D366V-I442V-G627D-C636S | 4.5 |
| 39 | H554Q-F572L-F624L | 12.2 |

TABLE 1B-continued

Summary of specificity of Are2 variants based on several independent experiments. The number indicates the x-times increase in the percentage of 7-DHC compared to the percentage of zymosterol in the sterol mx generated using the indicated amino acids exchange instead of a wild-type ARE2. For more explanation, see text.

| # | AA exchange(s) | Specificity |
|---|----------------|-------------|
| 40 | H554Q-F572L-G627D | 5.0 |
| 41 | I442V-F624L-L626F | 3.1 |
| 42 | I442V-L626F-G627D | 2.2 |
| 43 | I442V-G627D | 3.5 |

TABLE 1C

Summary of total 7-DHC production of Are2 variants based on several independent experiments. The number indicates the x-times increase in the total amount of produced 7-DHC generated using the indicated amino acids exchange instead of a wild-type ARE2. For more explanation, see text.

| # | AA exchange(s) | Total 7-DHC production |
|---|----------------|-----------------------|
| 1 | H554Q | 1.0 |
| 20 | F624L | 1.0 |

TABLE 1C-continued

Summary of total 7-DHC production of Are2 variants based on several independent experiments. The number indicates the x-times increase in the total amount of produced 7-DHC generated using the indicated amino acids exchange instead of a wild-type ARE2. For more explanation, see text.

| # | AA exchange(s) | Total 7-DHC production |
|---|----------------|-----------------------|
| 22 | G627D | 1.0 |
| 24 | I442V-L626F | 1.3 |
| 27 | E11G-D366V-C636S | 1.2 |
| 32 | E11G-D366V-F624L-C636S | 1.4 |
| 33 | E11G-D366V-F624L-C636S | 1.4 |
| 34 | E11G-D366V-G627D-C636S | 1.3 |
| 35 | E11G-F624L | 1.1 |
| 36 | E11G-G627D | 1.1 |
| 37 | E11G-D366V-I442V-F624L-C636S | 1.4 |
| 38 | E11G-D366V-I442V-G627D-C636S | 1.1 |
| 39 | H554Q-F572L-F624L | 1.0 |
| 40 | H554Q-F572L-G627D | 1.3 |
| 41 | I442V-F624L-L626F | 1.4 |
| 42 | I442V-L626F-G627D | 1.4 |
| 43 | I442V-G627D | 1.4 |

The invention claimed is:

1. A modified enzyme having sterol acyltransferase activity, comprising at least 99% identity to SEQ ID NO: 1 and one or more amino acid substitution(s) at (a) position(s) corresponding to residues selected from the group consisting of 11, 281, 366, 442, 551, 554, 572, 624, 626, 627, and 636 in the polypeptide according to SEQ ID NO: 1, wherein the one or more amino acid substitution(s) is/are selected from the group consisting of:

L281I,
H554Q,
F624L,
G627D,
E11G-F624L,
E11G-G627D,
I442V-G627D,
I442V-L626F,
H551Y-F572L,
H554Q-F572L,
E11G-D366V-C636S,
I442V-F624L-L626F,
I442V-L626F-G627D,
H554Q-F572L-F624L,
H554Q-F572L-G627D,
E11G-D366V-F624L-C636S,
E11G-D366V-G627D-C636S,
E11G-D366V-I442V-F624L-C636S, and
E11G-D366V-I442V-G627D-C636S.

2. The modified enzyme according to claim 1, wherein the one or more amino acid substitution(s) is/are selected from the group of substitutions consisting of:

I442V-L626F,
E11G-D366V-C636S,
E11G-D366V-F624L-C636S,
E11G-D366V-G627D-C636S,
E11G-F624L,
E11G-G627D,
E11G-D366V-I442V-F624L-C636S,
E11G-D366V-I442V-G627D-C636S,
H554Q-F572L-F624L,
H554Q-F572L-G627D,
I442V-F624L-L626F,
I442V-L626F-G627D, and
I442V-G627D.

3. A yeast host cell, comprising the modified enzyme according to claim 1.

4. The yeast host cell according to claim 3, further comprising a modified enzyme with at least 99.6% identity to SEQ ID NO: 3 and one or more amino acid substitution(s) at (a) position(s) corresponding to residues selected from 592 and/or 595.

5. The yeast host cell according to claim 3, wherein ERG5 gene and ERG6 gene are inactivated.

6. The yeast host cell according to claim 3, wherein the cell expresses a heterologous enzyme selected from EC 1.3.1.72 having sterol Δ24-reductase activity.

7. A process for reducing the percentage of zymosterol in a sterol mix comprising zymosterol and 7-dehydrocholesterol (7-DHC) comprising cultivating the yeast host cell according to claim 3 under suitable conditions, wherein the yeast host cell is *Saccharomyces cerevisiae*.

8. A process for producing 7-dehydrocholesterol (7-DHC) comprising cultivating the yeast host cell according to claim 3 under suitable conditions, wherein the yeast host cell is *Saccharomyces cerevisiae*, wherein acetyl-CoA is converted into a sterol mix comprising zymosterol and 7-DHC, and wherein the percentage of 7-DHC in the sterol mix is at least 40%.

9. The process according to claim 8, wherein the 7-DHC is further converted into vitamin D3.

10. The process according to claim 8, wherein the 7-DHC is further converted into 25-hydroxyvitamin D3.

11. The yeast host cell according to claim 3, which is a sterol-producing yeast.

12. The yeast host cell according to claim 3, which is a cholesterol-producing yeast.

13. The yeast host cell according to claim 4, wherein the one or more amino acid substitutions are F592L and/or G595D.

14. The yeast host cell according to claim 6, wherein the heterologous enzyme having sterol Δ24-reductase activity is a plant or vertebrate enzyme having sterol Δ24-reductase activity.

15. The yeast host cell according to claim 6, wherein the heterologous enzyme having sterol Δ24-reductase activity is a human, pig, dog, mouse, rat, or horse enzyme having sterol Δ24-reductase activity.

16. The yeast host cell according to claim 6, wherein the heterologous enzyme having sterol Δ24-reductase activity is a *Danio rerio* enzyme having sterol Δ24-reductase activity.

17. A modified enzyme having sterol acyltransferase activity, comprising the amino acid sequence of SEQ ID NO: 1 and one or more amino acid substitution(s) at (a) position(s) corresponding to residues selected from the group consisting of 11, 281, 366, 442, 551, 554, 572, 624, 626, 627, and 636 in the polypeptide according to SEQ ID NO: 1, wherein the one or more amino acid substitution(s) is/are selected from the group consisting of:

L281I,

H554Q,

F624L,

G627D,

E11G-F624L,

E11G-G627D,

I442V-G627D,

I442V-L626F,

H551Y-F572L,

H554Q-F572L,

E11G-D366V-C636S,

I442V-F624L-L626F,

I442V-L626F-G627D,

H554Q-F572L-F624L,

H554Q-F572L-G627D,

E11G-D366V-F624L-C636S,

E11G-D366V-G627D-C636S,

E11G-D366V-I442V-F624L-C636S, and

E11G-D366V-I442V-G627D-C636S.

18. The modified enzyme according to claim 17, wherein the one or more amino acid substitution(s) is/are selected from the group of substitutions consisting of:

I442V-L626F,

E11G-D366V-C636S,

E11G-D366V-F624L-C636S,

E11G-D366V-G627D-C636S,

E11G-F624L,

E11G-G627D,

E11G-D366V-I442V-F624L-C636S,

E11G-D366V-I442V-G627D-C636S,

H554Q-F572L-F624L,

H554Q-F572L-G627D,

I442V-F624L-L626F,

I442V-L626F-G627D, and

I442V-G627D.

19. A yeast host cell, comprising the modified enzyme according to claim 17.

* * * * *

```
                        SEQUENCE LISTING

<160> NUMBER OF SEQ ID NOS: 8

<210> SEQ ID NO 1
<211> LENGTH: 642
<212> TYPE: PRT
<213> ORGANISM: Saccharomyces cerevisiae

<400> SEQUENCE: 1

Met Asp Lys Lys Lys Asp Leu Leu Glu Asn Glu Gln Phe Leu Arg Ile
1               5                   10                  15

Gln Lys Leu Asn Ala Ala Asp Ala Gly Lys Arg Gln Ser Ile Thr Val
                20                  25                  30

Asp Asp Glu Gly Glu Leu Tyr Gly Leu Asp Thr Ser Gly Asn Ser Pro
            35                  40                  45

Ala Asn Glu His Thr Ala Thr Thr Ile Thr Gln Asn His Ser Val Val
        50                  55                  60

Ala Ser Asn Gly Asp Val Ala Phe Ile Pro Gly Thr Ala Thr Glu Gly
65                  70                  75                  80

Asn Thr Glu Ile Val Thr Glu Glu Val Ile Glu Thr Asp Asp Asn Met
                85                  90                  95

Phe Lys Thr His Val Lys Thr Leu Ser Ser Lys Glu Lys Ala Arg Tyr
            100                 105                 110

Arg Gln Gly Ser Ser Asn Phe Ile Ser Tyr Phe Asp Asp Met Ser Phe
            115                 120                 125

Glu His Arg Pro Ser Ile Leu Asp Gly Ser Val Asn Glu Pro Phe Lys
        130                 135                 140

Thr Lys Phe Val Gly Pro Thr Leu Glu Lys Glu Ile Arg Arg Arg Glu
145                 150                 155                 160

Lys Glu Leu Met Ala Met Arg Lys Asn Leu His His Arg Lys Ser Ser
                165                 170                 175

Pro Asp Ala Val Asp Ser Val Gly Lys Asn Asp Gly Ala Ala Pro Thr
            180                 185                 190
```

-continued

```
Thr Val Pro Thr Ala Ala Thr Ser Glu Thr Val Val Thr Val Glu Thr
        195                 200                 205

Thr Ile Ile Ser Ser Asn Phe Ser Gly Leu Tyr Val Ala Phe Trp Met
        210                 215                 220

Ala Ile Ala Phe Gly Ala Val Lys Ala Leu Ile Asp Tyr Tyr Tyr Gln
225                 230                 235                 240

His Asn Gly Ser Phe Lys Asp Ser Glu Ile Leu Lys Phe Met Thr Thr
                245                 250                 255

Asn Leu Phe Thr Val Ala Ser Val Asp Leu Leu Met Tyr Leu Ser Thr
                260                 265                 270

Tyr Phe Val Val Gly Ile Gln Tyr Leu Cys Lys Trp Gly Val Leu Lys
                275                 280                 285

Trp Gly Thr Thr Gly Trp Ile Phe Thr Ser Ile Tyr Glu Phe Leu Phe
        290                 295                 300

Val Ile Phe Tyr Met Tyr Leu Thr Glu Asn Ile Leu Lys Leu His Trp
305                 310                 315                 320

Leu Ser Lys Ile Phe Leu Phe Leu His Ser Leu Val Leu Leu Met Lys
                325                 330                 335

Met His Ser Phe Ala Phe Tyr Asn Gly Tyr Leu Trp Gly Ile Lys Glu
                340                 345                 350

Glu Leu Gln Phe Ser Lys Ser Ala Leu Ala Lys Tyr Lys Asp Ser Ile
        355                 360                 365

Asn Asp Pro Lys Val Ile Gly Ala Leu Glu Lys Ser Cys Glu Phe Cys
        370                 375                 380

Ser Phe Glu Leu Ser Ser Gln Ser Leu Ser Asp Gln Thr Gln Lys Phe
385                 390                 395                 400

Pro Asn Asn Ile Ser Ala Lys Ser Phe Phe Trp Phe Thr Met Phe Pro
                405                 410                 415

Thr Leu Ile Tyr Gln Ile Glu Tyr Pro Arg Thr Lys Glu Ile Arg Trp
                420                 425                 430

Ser Tyr Val Leu Glu Lys Ile Cys Ala Ile Phe Gly Thr Ile Phe Leu
                435                 440                 445

Met Met Ile Asp Ala Gln Ile Leu Met Tyr Pro Val Ala Met Arg Ala
        450                 455                 460

Leu Ala Val Arg Asn Ser Glu Trp Thr Gly Ile Leu Asp Arg Leu Leu
465                 470                 475                 480

Lys Trp Val Gly Leu Leu Val Asp Ile Val Pro Gly Phe Ile Val Met
                485                 490                 495

Tyr Ile Leu Asp Phe Tyr Leu Ile Trp Asp Ala Ile Leu Asn Cys Val
                500                 505                 510

Ala Glu Leu Thr Arg Phe Gly Asp Arg Tyr Phe Tyr Gly Asp Trp Trp
        515                 520                 525

Asn Cys Val Ser Trp Ala Asp Phe Ser Arg Ile Trp Asn Ile Pro Val
        530                 535                 540

His Lys Phe Leu Leu Arg His Val Tyr His Ser Ser Met Ser Ser Phe
545                 550                 555                 560

Lys Leu Asn Lys Ser Gln Ala Thr Leu Met Thr Phe Phe Leu Ser Ser
                565                 570                 575

Val Val His Glu Leu Ala Met Tyr Val Ile Phe Lys Lys Leu Arg Phe
                580                 585                 590

Tyr Leu Phe Phe Phe Gln Met Leu Gln Met Pro Leu Val Ala Leu Thr
        595                 600                 605

Asn Thr Lys Phe Met Arg Asn Arg Thr Ile Ile Gly Asn Val Ile Phe
```

```
           610                615                620
Trp Leu Gly Ile Cys Met Gly Pro Ser Val Met Cys Thr Leu Tyr Leu
625                630                635                640

Thr Phe

<210> SEQ ID NO 2
<211> LENGTH: 1929
<212> TYPE: DNA
<213> ORGANISM: Saccharomyces cerevisiae

<400> SEQUENCE: 2
atggacaaga agaaggatct actggagaac gaacaatttc tccgcatcca aaagctcaac      60
gctgccgatg cgggcaaaag acaatctata acagtggacg acgagggcga actatatggg     120
ttagacacct ccggcaactc accagccaat gaacacacag ctaccacaat tacacagaat     180
cacagcgtgg tggcctcaaa cggagacgtc gcattcatcc aggaactgc  taccgaaggc     240 aatacagaga ttgtaactga agaagtgatt gagaccgatg ataacatgtt caagacccat     300
gtgaagactt taagctccaa agagaaggca cggtataggc aagggtcctc aactttata     360 tcgtatttcg atgatatgtc atttgaacac aggcccagta tattagatgg gtcagttaac     420
gagcccttca gaccaaatt  cgtgggacct actttagaaa aggagatcag aagaagggag     480
aaagagctaa tggccatgcg caaaaattta caccaccgca agtcctcccc agatgctgtc     540
gactcagtag ggaaaaatga tggcgccgcc ccaactactg ttccaactgc cgccacctca     600
gaaacggtgg tcaccgttga aaccaccata atttcatcca atttctccgg gttgtacgtg     660 gcgtttttgga tggctattgc atttggtgct gtcaaggctt aatagacta ttattaccag      720 cataatggta gcttcaagga ttcggagatc ttgaaattta tgactacgaa tttgttcact     780
gtggcatccg tagatctttt gatgtatttg agcacttatt ttgtcgttgg aatacaatac     840
ttatgcaagt gggggtcttt gaaatggggc actaccggct ggatcttcac ctcaatttac     900
gagtttttgt ttgttatctt ctacatgtat ttaacagaaa acatcctaaa actacactgg     960
ctgtccaaga tcttcctttt tttgcattct ttagttttat tgatgaaaat gcattctttc    1020
gccttctaca atggctatct atggggtata aaggaagaac tacaattttc caaaagcgct    1080
cttgccaaat acaaggattc tataaatgat ccaaaagtta ttggtgctct tgagaaaagc    1140
tgtgagtttt gtagttttga attgagctct cagtctttaa gcgaccaaac tcaaaaattc    1200
cccaacaata tcagtgcaaa aagctttttt tggttcacca tgtttccaac cctaatttac    1260
caaattgaat atccaagaac taaggaaatc agatggagct acgtattaga aaagatctgc    1320
gccatcttcg gtaccatttt cttaatgatg atagatgctc aaatcttgat gtatcctgta    1380
gcaatgagag cattggctgt gcgcaattct gaatggactg gtatattgga tagattattg    1440
aaatgggttg gattgctcgt tgatatcgtc ccagggttta tcgtgatgta catcttggac    1500
ttctatttga tttgggatgc cattttgaac tgtgtggctg aattgacaag atttggcgac    1560
agatatttct acggtgactg gtggaattgt gttagttggg cagacttcag tagaatttgg    1620
aacatcccag tgcataagtt tttgttaaga catgtttacc atagttcaat gagttcattc    1680
aaattgaaca gagtcaagc  aactttgatg acctttttct taagttccgt cgttcatgaa    1740
ttagcaatgt acgttatctt caagaaattg aggtttact  tgttcttctt ccaaatgctg    1800
caaatgccat tagtagcttt aacaaatact aaattcatga ggaacagaac cataatcgga    1860
aatgttattt tctggctcgg tatctgcatg ggaccaagtg tcatgtgtac gttgtacttg    1920
```

-continued acattctaa                                                                        1929

<210> SEQ ID NO 3
<211> LENGTH: 610
<212> TYPE: PRT
<213> ORGANISM: Saccharomyces cerevisiae

<400> SEQUENCE: 3

Met Thr Glu Thr Lys Asp Leu Leu Gln Asp Glu Glu Phe Leu Lys Ile
1               5                   10                  15

Arg Arg Leu Asn Ser Ala Glu Ala Asn Lys Arg His Ser Val Thr Tyr
            20                  25                  30

Asp Asn Val Ile Leu Pro Gln Glu Ser Met Glu Val Ser Pro Arg Ser
        35                  40                  45

Ser Thr Thr Ser Leu Val Glu Pro Val Glu Ser Thr Glu Gly Val Glu
    50                  55                  60

Ser Thr Glu Ala Glu Arg Val Ala Gly Lys Gln Glu Gln Glu Glu Glu
65                  70                  75                  80

Tyr Pro Val Asp Ala His Met Gln Lys Tyr Leu Ser His Leu Lys Ser
                85                  90                  95

Lys Ser Arg Ser Arg Phe His Arg Lys Asp Ala Ser Lys Tyr Val Ser
            100                 105                 110

Phe Phe Gly Asp Val Ser Phe Asp Pro Arg Pro Thr Leu Leu Asp Ser
            115                 120                 125

Ala Ile Asn Val Pro Phe Gln Thr Thr Phe Lys Gly Pro Val Leu Glu
        130                 135                 140

Lys Gln Leu Lys Asn Leu Gln Leu Thr Lys Thr Lys Thr Lys Ala Thr
145                 150                 155                 160

Val Lys Thr Thr Val Lys Thr Thr Glu Lys Thr Asp Lys Ala Asp Ala
                165                 170                 175

Pro Pro Gly Glu Lys Leu Glu Ser Asn Phe Ser Gly Ile Tyr Val Phe
                180                 185                 190

Ala Trp Met Phe Leu Gly Trp Ile Ala Ile Arg Cys Cys Thr Asp Tyr
            195                 200                 205

Tyr Ala Ser Tyr Gly Ser Ala Trp Asn Lys Leu Glu Ile Val Gln Tyr
        210                 215                 220

Met Thr Thr Asp Leu Phe Thr Ile Ala Met Leu Asp Leu Ala Met Phe
225                 230                 235                 240

Leu Cys Thr Phe Phe Val Val Phe Val His Trp Leu Val Lys Lys Arg
                245                 250                 255

Ile Ile Asn Trp Lys Trp Thr Gly Phe Val Ala Val Ser Ile Phe Glu
            260                 265                 270

Leu Ala Phe Ile Pro Val Thr Phe Pro Ile Tyr Val Tyr Tyr Phe Asp
            275                 280                 285

Phe Asn Trp Val Thr Arg Ile Phe Leu Phe Leu His Ser Val Val Phe
        290                 295                 300

Val Met Lys Ser His Ser Phe Ala Phe Tyr Asn Gly Tyr Leu Trp Asp
305                 310                 315                 320

Ile Lys Gln Glu Leu Glu Tyr Ser Ser Lys Gln Leu Gln Lys Tyr Lys
                325                 330                 335

Glu Ser Leu Ser Pro Glu Thr Arg Glu Ile Leu Gln Lys Ser Cys Asp
            340                 345                 350

Phe Cys Leu Phe Glu Leu Asn Tyr Gln Thr Lys Asp Asn Asp Phe Pro
            355                 360                 365

-continued

```
Asn Asn Ile Ser Cys Ser Asn Phe Phe Met Phe Cys Leu Phe Pro Val
    370                 375                 380

Leu Val Tyr Gln Ile Asn Tyr Pro Arg Thr Ser Arg Ile Arg Trp Arg
385                 390                 395                 400

Tyr Val Leu Glu Lys Val Cys Ala Ile Ile Gly Thr Ile Phe Leu Met
                405                 410                 415

Met Val Thr Ala Gln Phe Phe Met His Pro Val Ala Met Arg Cys Ile
                420                 425                 430

Gln Phe His Asn Thr Pro Thr Phe Gly Gly Trp Ile Pro Ala Thr Gln
            435                 440                 445

Glu Trp Phe His Leu Leu Phe Asp Met Ile Pro Gly Phe Thr Val Leu
        450                 455                 460

Tyr Met Leu Thr Phe Tyr Met Ile Trp Asp Ala Leu Leu Asn Cys Val
465                 470                 475                 480

Ala Glu Leu Thr Arg Phe Ala Asp Arg Tyr Phe Tyr Gly Asp Trp Trp
                485                 490                 495

Asn Cys Val Ser Phe Glu Glu Phe Ser Arg Ile Trp Asn Val Pro Val
                500                 505                 510

His Lys Phe Leu Leu Arg His Val Tyr His Ser Ser Met Gly Ala Leu
            515                 520                 525

His Leu Ser Lys Ser Gln Ala Thr Leu Phe Thr Phe Phe Leu Ser Ala
        530                 535                 540

Val Phe His Glu Met Ala Met Phe Ala Ile Phe Arg Arg Val Arg Gly
545                 550                 555                 560

Tyr Leu Phe Met Phe Gln Leu Ser Gln Phe Val Trp Thr Ala Leu Ser
                565                 570                 575

Asn Thr Lys Phe Leu Arg Ala Arg Pro Gln Leu Ser Asn Val Val Phe
                580                 585                 590

Ser Phe Gly Val Cys Ser Gly Pro Ser Ile Ile Met Thr Leu Tyr Leu
            595                 600                 605

Thr Leu
    610
```

<210> SEQ ID NO 4
<211> LENGTH: 1833
<212> TYPE: DNA
<213> ORGANISM: Saccharomyces cerevisiae

<400> SEQUENCE: 4

```
atgacggaga ctaaggattt gttgcaagac gaagagtttc ttaagatccg cagactcaat      60
tccgcagaag ccaacaaacg gcattcggtc acgtacgata acgtgatcct gccacaggag     120
tccatggagg tttcgccacg gtcgtctacc acgtcgctgg tggagccagt ggagtcgact     180
gaaggagtgg agtcgactga ggcggaacgt gtggcaggga agcaggagca ggaggaggag     240
taccctgtgg acgcccacat gcaaaagtac ctttcacacc tgaagagcaa gtctcggtcg     300
aggttccacc gaaaggatgc tagcaagtat gtgtcgtttt tggggacgt gagttttgat     360 cctcgcccca cgctcctgga cagcgccatc aacgtgccct ccagacgac tttcaaaggt     420 ccggtgctgg agaaacagct caaaaattta cagttgacaa agaccaagac caaggccacg     480
gtgaagacta cggtgaagac tacggagaaa acggacaagg cagatgcccc cccaggagaa     540
aaactggagt cgaacttttc agggatctac gtgttcgcat ggatgttctt gggctggata     600
gccatcaggt gctgcacaga ttactatgcg tcgtacggca gtgcatggaa taagctggaa     660
atcgtgcagt acatgacaac ggacttgttc acgatcgcaa tgttggactt ggcaatgttc     720
```

-continued

```
ctgtgcactt tcttcgtggt tttcgtgcac tggctggtga aaaagcggat catcaactgg     780
aagtggactg ggttcgttgc agtgagcatc ttcgagttgg ctttcatccc cgtgacgttc     840
cccatttacg tctactactt tgatttcaac tgggtcacga gaatcttcct gttcctgcac     900
tccgtggtgt ttgttatgaa gagccactcg tttgcctttt acaacgggta tctttgggac     960
ataaagcagg aactcgagta ctcttccaaa cagttgcaaa aatacaagga atctttgtcc    1020
ccagagaccc gcgagattct gcaaaaaagt tgcgactttt gcctttTcga attgaactac    1080
cagaccaagg ataacgactt ccccaacaac atcagttgca gcaatttctt catgttctgt    1140
ttgttccccg tcctcgtgta ccagatcaac tacccaagaa cgtcgcgcat cagatggagg    1200
tatgtgttgg agaaggtgtg cgccatcatt ggcaccatct tcctcatgat ggtcacggca    1260
cagttcttca tgcacccggt ggccatgcgc tgtatccagt tccacaacac gcccaccttc    1320
ggcggctgga tccccgccac gcaagagtgg ttccacctgc tcttcgacat gattccgggc    1380
ttcactgttc tgtacatgct cacgttttac atgatatggg acgctttatt gaattgcgtg    1440
gcggagttga ccaggtttgc ggacagatat ttctacggcg actggtggaa ttgcgtttcg    1500
tttgaagagt ttagcagaat ctggaacgtc cccgttcaca aattttttact aagacacgtg    1560 taccacagct ccatgggcgc attgcatttg agcaagagcc aagctacatt atttacttttt    1620 ttcttgagtg ccgtgttcca cgaaatggcc atgttcgcca ttttcagaag ggttagagga    1680
tatctgttca tgttccaact gtcgcagttt gtgtggactg ctttgagcaa caccaagttt    1740
ctacgggcaa gaccgcagtt gtccaacgtt gtcttttcgt ttggtgtctg ttcagggccc    1800
agtatcatta tgacgttgta cctgaccta tga                                  1833
```

```
<210> SEQ ID NO 5
<211> LENGTH: 241
<212> TYPE: PRT
<213> ORGANISM: Ustilago maydis

<400> SEQUENCE: 5

Met Ala Ser His Arg Pro Arg Ser Asn Lys Ala Ala Asn Gly Ala Ser
1               5                   10                  15

Thr Ser Pro Lys Arg Ser Trp Ile Ile Val Ser Ala Ala Leu Val Gly
            20                  25                  30

Phe Cys Ala Leu Ile Ala Ala Leu Asp Ser Ile Arg Ser Ser Phe Tyr
        35                  40                  45

Ile Phe Asp His Lys Ala Ile Tyr Lys Ile Ala Ser Thr Ala Val Ala
    50                  55                  60

Asn His Pro Gly Asn Ala Thr Ala Ile Phe Asp Asp Val Leu Asp Asn
65                  70                  75                  80

Leu Arg Ala Asp Pro Lys Leu Ala Pro Tyr Ile Asn Lys Asn His Phe
                85                  90                  95

Ser Asp Glu Ser Glu Trp Met Phe Asn Asn Ala Gly Gly Ala Met Gly
            100                 105                 110

Ser Met Phe Ile Ile His Ala Ser Val Thr Glu Tyr Leu Ile Phe Phe
        115                 120                 125

Gly Thr Pro Val Gly Thr Glu Gly His Thr Gly Arg His Thr Ala Asp
        130                 135                 140

Asp Tyr Phe Asn Ile Leu Thr Gly Asn Gln Tyr Ala Phe Pro Ala Gly
145                 150                 155                 160

Ala Leu Lys Ala Glu His Tyr Pro Ala Gly Ser Val His His Leu Arg
                165                 170                 175
```

Arg Gly Thr Val Lys Gln Tyr Met Met Pro Glu Asp Gly Cys Trp Ala
            180                 185                 190

Leu Glu Leu Ala Gln Gly Trp Ile Pro Pro Met Leu Pro Phe Gly Leu
            195                 200                 205

Ala Asp Val Leu Ser Ser Thr Leu Asp Leu Pro Thr Phe Gly Ile Thr
    210                 215                 220

Val Trp Ile Thr Ala Arg Glu Met Val Gly Asn Leu Leu Ile Gly Lys
225                 230                 235                 240

Phe

<210> SEQ ID NO 6
<211> LENGTH: 726
<212> TYPE: DNA
<213> ORGANISM: Ustilago maydis

<400> SEQUENCE: 6
atggcatcgc atagaccacg cagcaacaag gctgccaatg gtgcttcgac ttcacccaaa        60
cgcagctgga taattgtctc agctgcgctc gttggcttct gcgctctcat cgccgctctc       120
gattcgatcc gatccagctt ctacatcttt gaccacaagg caatctacaa gatcgcatcg       180
actgcggtcg ccaaccatcc aggcaatgcg acggccatct ttgatgatgt cctcgacaac       240
cttcgtgccg accccaagct cgcgccttac atcaacaaga tcatttcag cgacgagtca        300 gaatggatgt tcaacaatgc cggtggtgct atgggtagca tgttcatcat tcatgcttcc       360
gtcaccgagt acctgatctt ctttggcact cccgtcggaa ccgagggtca cactggtcgt       420
cacacagccg atgactactt caacatcctt accggtaacc aatacgcttt cccagctggt       480
gcgctcaagg cggagcacta ccctgccgga tcagtgcacc atcttcgccg cggaacggtc       540
aagcagtaca tgatgcctga agacggctgc tgggcgctcg agcttgctca gggctggatc       600
ccacccatgc ttccctttgg tctcgccgat gtgctcagct cgacgctcga cctgcccacc       660
tttggtatca ctgtctggat cactgcacga gaaatggttg gcaatctgct catcggcaag       720
ttttga                                                                   726

<210> SEQ ID NO 7
<211> LENGTH: 384
<212> TYPE: PRT
<213> ORGANISM: Pichia pastoris

<400> SEQUENCE: 7

Met Asp Ile Ala Leu Glu Ile Leu Asp Thr Phe Val Phe Asp Lys Val
1               5                   10                  15

Tyr Ala Lys Leu Leu Pro Ile Ser Leu Val Gln His Leu Pro Asp Gly
            20                  25                  30

Tyr Leu Lys Thr Leu Gly His Leu Thr Gly Ala Asn Asn Thr Met Glu
        35                  40                  45

Ser Leu Phe Gly Ile Ala Pro Asn Val Asp Gln Ala Ser Lys Asn His
    50                  55                  60

Trp Leu Arg Thr Val Asn Asp Ser Ile Ala Leu Ala Arg Pro Gly Glu
65                  70                  75                  80

Arg Leu Val Tyr Gly Val Asn Ala Pro Leu His Phe Phe Asp Glu Thr
                85                  90                  95

Ala Tyr Thr Tyr Ala Ser Ile Leu Gly Arg Ser Asn Ile Ile Arg Gln
            100                 105                 110

Phe Thr Thr Leu Met Ile Leu Met Ile Leu Phe Gly Trp Gly Leu Tyr

-continued

```
          115               120               125
Leu Ser Val Ala Ser Phe Ser Tyr Tyr Phe Val Phe Asp Lys Ala Ile
    130               135               140

Phe Asn His Pro Arg Tyr Leu Lys Asn Gln Met Ser Leu Glu Ile His
145               150               155               160

Gln Ala Leu Thr Ala Ile Pro Thr Met Val Leu Leu Thr Val Pro Trp
                165               170               175

Phe Leu Ile Glu Leu Arg Gly Tyr Ser Lys Leu Tyr Phe Asp Val Asn
                180               185               190

Glu Ser Thr Gly Gly Trp Lys Ala Ile Ile Trp Gln Ile Pro Cys Phe
                195               200               205

Ile Met Phe Thr Asp Cys Cys Ile Tyr Phe Ile His Arg Trp Leu His
    210               215               220

Trp Pro Ser Val Tyr Lys Arg Leu His Lys Pro His His Lys Trp Ile
225               230               235               240

Val Cys Thr Pro Phe Ala Ser His Ala Phe His Pro Val Asp Gly Tyr
                245               250               255

Ala Gln Ser Leu Pro Tyr His Leu Tyr Gly Met Leu Phe Pro Leu His
                260               265               270

Lys Val Ser Tyr Leu Ile Leu Phe Gly Leu Val Asn Phe Trp Thr Val
    275               280               285

Met Ile His Asp Gly Glu Tyr Leu Ser Arg Asp Pro Ile Val Asn Gly
    290               295               300

Ala Ala Cys His Thr Val His His Leu Tyr Phe Asn Tyr Asn Tyr Gly
305               310               315               320

Gln Phe Thr Thr Leu Trp Asp Arg Leu Gly Gly Ser Tyr Arg Met Pro
                325               330               335

Asp Lys Glu Leu Phe Asp Lys Asn Lys Lys Lys Asp Val Lys Thr Trp
                340               345               350

Arg Ser Gln Val Lys Gln Ala Asp Ser Ile Arg Glu Asp Leu Glu Gly
        355               360               365

Lys Glu Asp Phe Arg Glu Tyr Gly Thr Glu Glu Lys Leu Lys Ser Thr
    370               375               380
```

```
<210> SEQ ID NO 8
<211> LENGTH: 1155
<212> TYPE: DNA
<213> ORGANISM: Pichia pastoris

<400> SEQUENCE: 8
atggacattg ctttggagat ctagacact tttgtctttg acaaagtcta tgcaaaacta        60
ctgcccattt tctctggtgca acatttgcca gatggctatt tgaagacttt gggacatttg       120
actggtgcca acaacaccat ggaatcactg ttcggaatag ctccaaacgt tgaccaagcg       180
tctaagaacc actggctgag aacagtgaat gactctattg ccttagcccg tcccggtgag       240
cgtctggtct acggtgtcaa cgctcccttta cacttttttg acgaaacagc gtatacatac       300
gcatcgatct tgggacgctc caatatcatt cgacaattca caactttgat gattctgatg       360 attcttttttg ctgggggttt gtatttatct gtggcttcat tttcatacta ctttgttttt       420
gataaagcca ttttcaatca cccaagatac ctcaaaaacc agatgtctct ggagatccat       480
caagcgttga ctgctatacc tacgatggtt ttgcttacag ttccatggtt tttgattgag       540
ttgcgtggat actctaaatt atactttgat gtaaatgagt ctactggagg atggaaggct       600
attatttggc aaattccttg cttcattatg tttaccgatt gttgtatcta ctttattcat       660
```

-continued

```
cgttggttgc actggccatc cgtgtataag cgtttgcaca agcctcacca caagtggatt    720
gtttgtacac cttttgctag tcatgccttc catccagttg atggttatgc acaatcacta    780
ccttaccatt tgtatggaat gttgtttcca ctacacaagg tgagctatct gatcttattt    840
gggcttgtga acttttggac tgttatgatc catgatggag aatacctgtc cagagaccct    900
atagtcaatg gagctgcttg tcatacagtg catcacctat acttcaacta caattacggc    960
cagttcacaa cactttggga ccgtcttggt ggatcataca gaatgccaga caaggaactc   1020
tttgataaga acaagaagaa agatgtaaag acatggcgtt cacaagtcaa gcaggccgat   1080
tcgataagag aagacttaga gggaaaagaa gatttccgtg agtatggaac tgaggaaaaa   1140
cttaaaagca catag                                                   1155
```